United States Patent [19]
Negulescu et al.

[11] Patent Number: 6,004,808
[45] Date of Patent: Dec. 21, 1999

[54] PROMISCUOUS G-PROTEIN COMPOSITIONS AND THEIR USE

[75] Inventors: Paul Negulescu, Solana Beach, Calif.; Stefan Offermanns, Berlin, Germany; Melvin Simon, San Marino; Charles Zuker, San Diego, both of Calif.

[73] Assignee: Aurora BioSciences Corporation, San Diego, Calif.

[21] Appl. No.: 08/878,801

[22] Filed: Jun. 19, 1997

Related U.S. Application Data

[60] Provisional application No. 60/020,234, Jun. 21, 1996.

[51] Int. Cl.$^6$ ..................... C12N 5/10
[52] U.S. Cl. .............. 435/325; 435/4; 435/172.3; 435/366; 436/63
[58] Field of Search ............ 435/325, 4, 172.3, 435/366; 436/63

[56] References Cited

U.S. PATENT DOCUMENTS

| | | | |
|---|---|---|---|
| 4,677,195 | 6/1987 | Hewick et al. | 530/397 |
| 4,703,008 | 10/1987 | Lin | 435/240.2 |
| 5,266,464 | 11/1993 | Housey | 435/29 |
| 5,273,999 | 12/1993 | Cohen et al. | 514/456 |
| 5,401,629 | 3/1995 | Harpold et al. | 435/6 |
| 5,462,856 | 10/1995 | Lerner et al. | 435/7.21 |
| 5,474,897 | 12/1995 | Weiss et al. | 435/6 |
| 5,580,722 | 12/1996 | Foulkes et al. | 435/6 |
| 5,665,543 | 9/1997 | Foulkes et al. | 435/6 |
| 5,691,188 | 11/1997 | Pausch et al. | 435/254.2 |
| 5,741,657 | 4/1998 | Tsien et al. | 435/18 |

FOREIGN PATENT DOCUMENTS

WO 93/07294 A1  4/1993  WIPO.

OTHER PUBLICATIONS

Qian et al., "Expression of GTPase–deficient $G_\alpha 16$ Inhibits Swiss 3T3 Cell Growth" The Journal of Biological Chemistry, 1994, vol. 269, No. 26, pp. 17417–17423, Jan. 7, 1994.

Chen et al. "Improved gene expression by a U3–based retroviral vector" Biochemical and Biophysical Research Communications, 1992, vol. 184, No. 1, pp. 330–337, Apr. 15, 1992.

Sternweis PC, et al. "Regulation of phospholipase C by G proteins." Trends Biochem Sci. Dec. 1992; 17(12):502–6. Review, Jan. 12, 1992.

Amatruda et al., J. Biol. Chem, 268:10139–10144 (1993).

Arai et al., J. Biol. Chem. 271–21814–21819 (1996).

Cerione et al. Biochemistry 23:4519–4525 (1984).

Conklin et al., Molecular Pharcology 50:885–890 (1996).

Freissmuth et al. Proc. Natl. Acad. Sci. USA 88:8548–8552 (1991).

George et all, Macromolecular Sequencing and Synthesis, Selected Methods and Applications, pp. 127–149 (1988).

Gomeza e al, Molecular Pharmacology 50:923–930 (1996).

Helper et al., J. Biol. chem. 268:14367–14375 (1993).

Hille, Trends in Neuroscience, 17:531–536 (1994).

Katzung, Basic and Clinical Pharmacology, fifth edition, Appleton &Lang, Conn (1992) p. 26.

Kozasa et al., Proc. Natl. Acad. Sci. USA 90:9176–9180 (1993).

Lee et al., J. Biol. Chem.287:16044–16047 (1992).

Luo et al.., Am. J. Physiol. 265(1 Pt 1):C193–200 (1993).

Neer, Cell, 80:249–257 (1995).

(List continued on next page.)

*Primary Examiner*—Ponnathapu Achutamurthy
*Assistant Examiner*—Bradley S. Mayhew
*Attorney, Agent, or Firm*—Gary Cary Ware & Freidenrich LLP; Lisa A. Haile

[57] ABSTRACT

Disclosed are compositions and methods for their use, such as in identifying G-protein coupled receptors and ligands and compounds that modulate signal transduction. The compositions and methods employ promicuous G-proteins. Activation of the promiscous G-protein can be detected in a variety of assays, including assays in which activation is indicated by a change in fluorescence emission of a sample that contains the composition.

27 Claims, 8 Drawing Sheets

OTHER PUBLICATIONS

Ngo et al., Computational Complexity, Protein Structure Prediction, and theLevinthal Paradox, in: The ProteinFolding Problem and Teritiary Structure Prediction, Merz adn Grand, eds, Birkhauser, Boston, Mass (1994).

Offermanns et al., Molecular Pharmacology 45:890–898 (1994).

Parker et al., J. Biol. chem. 266:519–527 (1991).

Rhee et al., J. Biol. Chem. 267–12393–12396 (1992).

Shapiro, Practical Flow Cytometry Third Edition, Wiley–Liss, N,Y. (1995), p. 223.

Simon et al., Science 252:802–808 (1991).

Stearns, Current Biology 5:262–264 (1995).

Sternweis et al., Trends in Biological Sciences, 17:502–506 (1992).

Strathmann et al., Proc. Natl. Acad. Sci. USA 87:9113–9117 No date provided.

Striessnig et al., Proc. Natl. Acad. Sci., 87:9108–9112 (1990).

Taussig et al., J. Biol. Chem. 270:1–4 (1995).

Wong et al., J. Biol. Chem. 269:18968–18976 (1994).

Wu et al., Science 261:101–103 (1993).

Wu et al., J. Biol. Chem. 267:25798–25802 (1992).

Wu et al., J. Biol. Chem. 267:1811–1817 (1992).

Wu et al., J. Biol. Chem. 270:16008–16010 (1995).

Mattila et al., "The Actions of cyclosporin A and FK506 suggest a novel step in the activiation of T Lymphocytes", The EMBO Journal, vol. 9, No. 13, pp. 4425–4433, 1990.

Arai et al., "Differential Regulation of G–protein–mediated Signaling by Chemokine Receptors", The Journal of BIological Chemistry, vol. 271, No. 36, Sep. 6, 1996, pp. 21814–21819.

Boss et al., "Induction of NFAT–mediated Transcription by $G_q$–coupled Receptors in Lymphoid and Non–lymphoid Cells", The Journal of BIological Chemistry, vol. 271, No. 18, May 3, 1996, pp. 10429–10432.

Wilkie et al., "Characterization of G–protein αsubunits in the $G_q$ class: Expression in murine tissues and in stromal and hematopoietic cell lines," Proc. Natl. Acad. Sci. USA, vol. 88, pp. 10049–10053, Nov. 1991.

Grossen et al., "Tight Control of Gene Expression in Mammalian Cells by Tetracycline–Responsive Promoters", Proc. Natl. Acad. Sci. USA, Jun. 1992, vol. 89, pp. 5547–5551.

Lee et al., "Members of the $G_q$ α Subunit Gene Family Activate Phospholipase C β Isozymes", The Journal of Biological Chemistryi, Aug. 15, 1992, vol. 267, No. 23, pp. 16044–16047.

Offermans et al., "$G\alpha_{15}$ and $G\alpha_{16}$ Couple a Wide Variety of Receptors to Phospolipase C", The Journal of Biological Chemistry, Jun. 23, 1995, vol. 270, No. 25, pp. 15175–15180.

Boss et al., J. Biol. Chem. 271:10429–10432 (1996).

Chen et al., Analyt. Biochem. 226:349–354 (1995).

Conklin et al., Mol. Pharmacol. 50:885–890 (1996).

Conklin et al., Nature, 363:274–276 (1993).

Goldsmith et al., J. Biol. Chem. 264:17190–17197 (1989).

Gomeza et al., Mol. Pharmacol. 50:923–930 (1996).

Hidenori et al., J. Biol. Chem. 271:21814–21819 (1996).

Mapara et al., Blood, 85:1836–1842 (1995).

Mattila et al., The EMBO J. 9:4425–4433 (1990).

Milligan et al., Trends in Pharmacol. Science, 17:235–237 (1996).

Offermanns and Simon, J. Biol. Chem., 270:15175–15180 (1995).

Wilkie et al., Proc. Natl. Acad. Sci. U.S.A., 88:10049–10053 (1991).

Wu et al., Mol. Cell Biol. 15:4337–4346 (1995).

France et al., Proceedings of the International Symposium on Laboratory Automation and Robotics, 1992, pp. 400–410.

Goddard et al., Proceedings of the International Symposium on Laboratory Automation and Robotics, 1992, pp. 392–399.

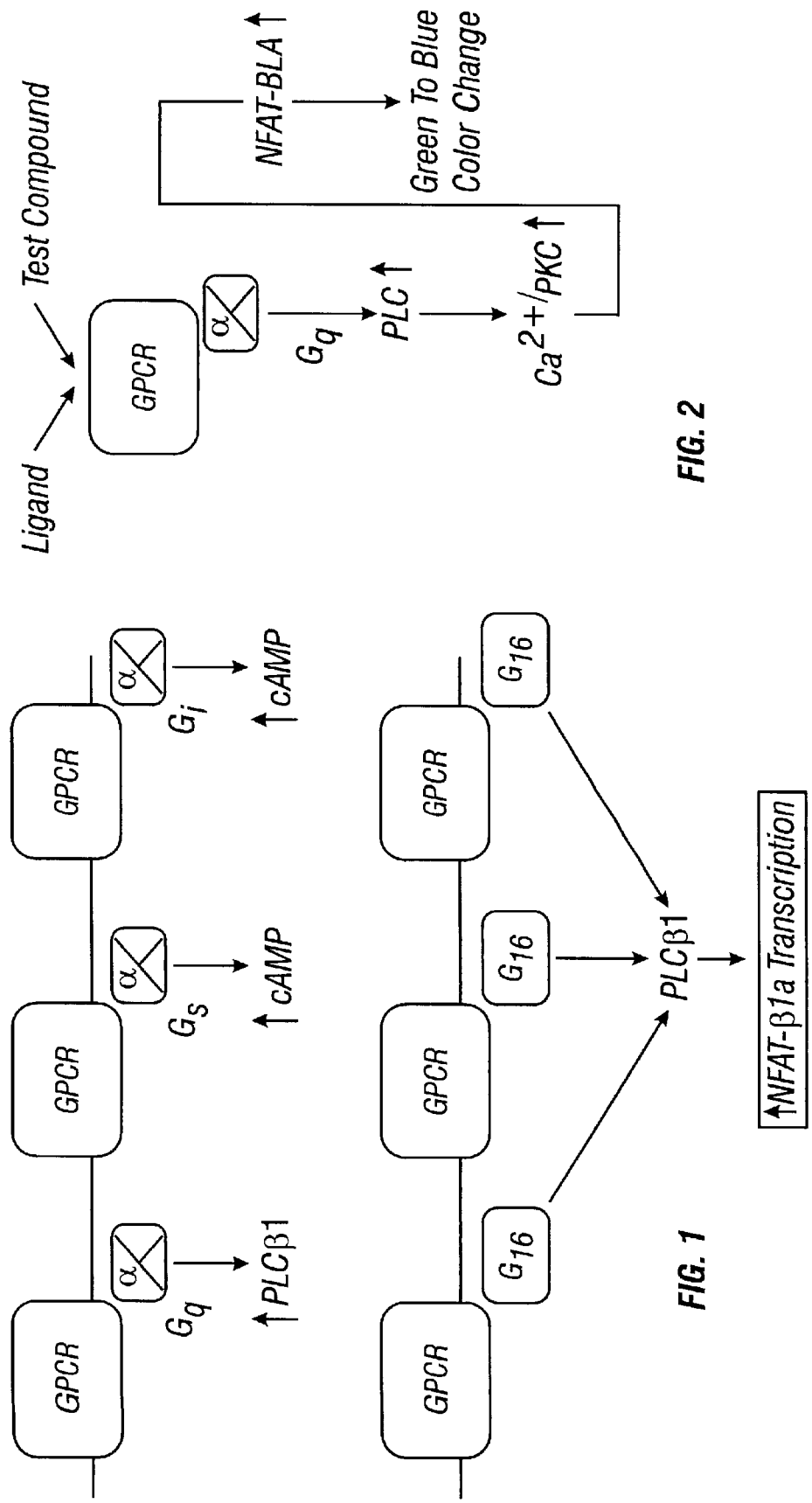

PROMISCUOUS G-PROTEIN COMPOSITIONS AND THEIR USE

CROSS REFERENCE TO RELATED APPLICATIONS

This application claims priority under 35 U.S.C. Section 119 to provisional patent application 60/020,234 filed on Jun. 21, 1996, by Negulescu et al., which is herein incorporated by reference and of which this application is a continuation.

FIELD OF THE INVENTION

The invention relates to compositions and methods for identifying G-protein coupled receptors (GPCRs) and compounds that modulate activity of G-proteins or their receptors.

BACKGROUND

Many physiological signals (e.g., sensory, hormonal and neurotransmitter signals) are transduced from extracellular to intracellular environments by cell surface receptors termed G-protein coupled receptors (GPCRs) (for a review, see Neer, 1995, Cell 80:249–257). Typically, GPCRs contain seven transmembrane domains. Putative GPCRs can be identified on the basis of sequence homology to known GPCRs.

GPCRs mediate signal transduction across a cell membrane upon the binding of a ligand to an extracellular portion of a GPCR. The intracellular portion of a GPCR interacts with a G-protein to modulate signal transduction from outside to inside a cell. A GPCR is therefore said to be "coupled" to a G-protein. G-proteins are composed of three polypeptide subunits: an α subunit, which binds and hydolyzes GTP, and a dimeric βγ subunit. In the basal, inactive state, the G-protein exists as a heterotrimer of the α and βγ subunits. When the G-protein is inactive, guanosine diphosphate (GDP) is associated with the α subunit of the G-protein. When a GPCR is bound and activated by a ligand, the GPCR binds to the G-protein heterotrimer and decreases the affinity of the Gα subunit for GDP. In its active state, the G subunit exchanges GDP for guanine triphosphate (GTP) and active Gα subunit disassociates from both the receptor and the dimeric βγ subunit. The disassociated, active Gα subunit transduces signals to effectors that are "downstream" in the G-protein signalling pathway within the cell. Eventually, the G-protein's endogenous GTPase activity returns active G subunit to its inactive state, in which it is associated with GDP and the dimeric βγ subunit.

Numerous members of the heterotrimeric G-protein family have been cloned, including more than 20 genes encoding various Gα subunits. The various G subunits have been categorized into four families, on the basis of amino acid sequences and functional homology. These four families are termed $G\alpha_s$, $G\alpha_i$, $G\alpha_q$, and $G\alpha_{12}$. Functionally, these four families differ with respect to the intracellular signaling pathways that they activate and the GPCR to which they couple.

For example, certain GPCRs normally couple with $G\alpha_s$ and, through $G\alpha_s$, these GPCRs stimulate adenylyl cyclase activity. Other GPCRs normally couple with $G\alpha_q$, and through $G\alpha_q$, these GPCRs can activate phospholipase C (PLC), such as the β isoform of phospholipase C (PLCβ) (Stermweis and Smrcka, 1992, Trends in Biochem. Sci. 17:502–506).

Certain G-proteins are considered "promiscuous" G-proteins because their G subunits allow them to couple with GPCRs that normally couple with G-proteins of other families. For example, two members of the $G\alpha_q$ family, human $G\alpha_{16}$ and its murine homolog $G\alpha_{15}$, have been shown in transient cell-based systems to possess promiscuous receptor coupling. Although G-proteins having these G subunits are promiscuous with respect to the GPCR with which they couple, these G-proteins retain the ability to couple with a specific downstream effector. In other words, regardless of which receptor is used to activate these G-proteins, the active promiscuous G subunit nonetheless activates PLCβ.

SUMMARY OF THE INVENTION

The invention provides for the first time, a stable, isolated cell that expresses, from a construct, a Gα subunit of a promiscuous G-protein (e.g., $G\alpha_{15}$ or $G\alpha_{16}$). In a preferred embodiment, a polynucleotide encoding a promiscuous G subunit is linked to an inducible promoter on the construct. To detect activation of the promiscuous G-protein, the cell can include an additional construct that includes a reporter gene operably linked to a promoter that is activated (usually indirectly) by an active G subunit of a promiscuous G-protein. For the first time, these cells allow occupation of any G-protein coupled receptor (GPCR) by a ligand to be detected using a signal transduction detection system, such as expression of a reporter gene. Other signal transduction detection systems include detecting changes in intracellular activity, such as methods of detecting G-protein activation from changes in calcium levels in the cell. Preferred methods for detecting expression of the reporter gene involve detecting a change in fluorescence emission from a sample that includes the cell containing the reporter gene.

Another key aspect of the invention is functional selection of stable cell lines. Stable cell lines can be functionally selected using a signal transduction detection system as described herein. Stable cells are generated that tolerate the expression of a target protein (such as an ion channel, kinase, phospholipase, phosphatase, transcription factors or GPCR) or a signal transduction coupling protein (e.g. G protein) or both.

The cells of the invention can be employed in methods for (i) determining whether a polypeptide is a GPCR for a given ligand; (ii) determining whether a "test" ligand is a ligand for a given GPCR; (iii) functionally characterizing the ability of a ligand to activate various GPCRs; and (iv) determining whether a compound modulates signal transduction in a cell (e.g., as an agonist or antagonist).

Another aspect of the invention includes, a method of a identifying of a ligand for a GPCR, the method comprising:
 a) contacting a cell with a test chemical, wherein said cell is expressing a GPCR and arises from a cell line subjected to functional cell analysis with a signal transduction detection system; and
 b) detecting a signal with a signal transduction detection system.

A related aspect of the invention includes, a method for identifying modulators of signal transduction in a cell, the method comprising:
 c) contacting a cell with a compound that directly or indirectly activates a Gα protein encoded by a polynucleotide, wherein said cell arises from a cell line subjected to functional cell analysis with a signal transduction detection system,
 d) contacting said cell with a test chemical, and
 e) detecting a signal with a signal transduction detection system.

The invention also includes, a method for identifying a GPCR for a given ligand or method of identifying a modulator of a GPCR, the method comprising:

f) expressing a putative GPCR or a GPCR of known function in a cell, wherein said cell arises from a cell line subjected to functional cell analysis with a signal transduction detection system;

g) contacting contacting said cell with a test chemical or a ligand known to be a GPCR ligand; and h) detecting a calcium level within said cell.

Also included within the invention, are kits that components for signal transduction detection systems and cells of the invention.

The invention also includes methods of identifying modulators that do not employ a GPCR, but which employ direct activators of G-proteins.

BRIEF DESCRIPTION OF THE DRAWINGS

FIG. 1: shows uses of promiscuous Gα-protein to detect activation of a variety of GPCRs. Three major classes of GPCRs are diagrammed coupling to their endogenous signaling cascade. Promiscuous G-protein expression will allow various classes to couple to the PLC cascade.

FIG. 2: shows one embodiment of the invention that can be used for screening for Gq type G-protein activation. Modulation of GPCR activity initiates signaling cascade via PLC. PLC signals can be detected using NFAT responsive element linked to a transcriptional readout (e.g. reporter gene).

FIG. 4B is a graph showing the PMA dose response of living cells that express a β-lactamase reporter gene, and which were contacted with a fluorogenic β-lactamase substrate. In this case, all samples were also treated with 2 μM ionomycin.

Panel A: 60 seconds after starting of the experiment, 10 μM agonist solution was added to the cells transfected by pCIS/Gα16 and Gs-receptor expression plasmids.

Panel B: 60 seconds after starting of the experiment, 10 μM agoinst solution was added to the cells transfected by both pCIS/Gα16 alone.

Panel C: 60 seconds after starting of the experiment, 10 μM agonist solution was added to the cells transfected by Gαs receptor expression plasmid alone.

Panel D: 60 seconds after starting of the experiment, 10 μM agonist solution was added to the cells transfected by pCIS/Gα16 and Gαi-receptor expression plasmids.

Panel E: 60 seconds after starting of the experiment, 10 μM agonist solution was added to the cells transfected by pCIS/Gα16 alone.

Panel F: 60 seconds after starting of the experiment, 10 μM agonist solution was added to the cells transfected by Gαi-receptor expression plasmid alone.

Figure 8A:
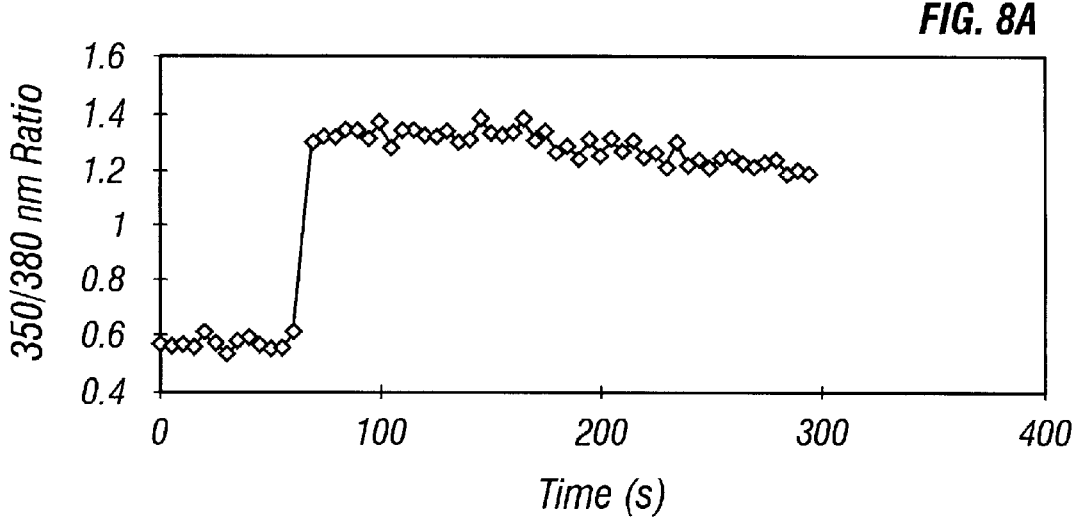
Figure 8B:
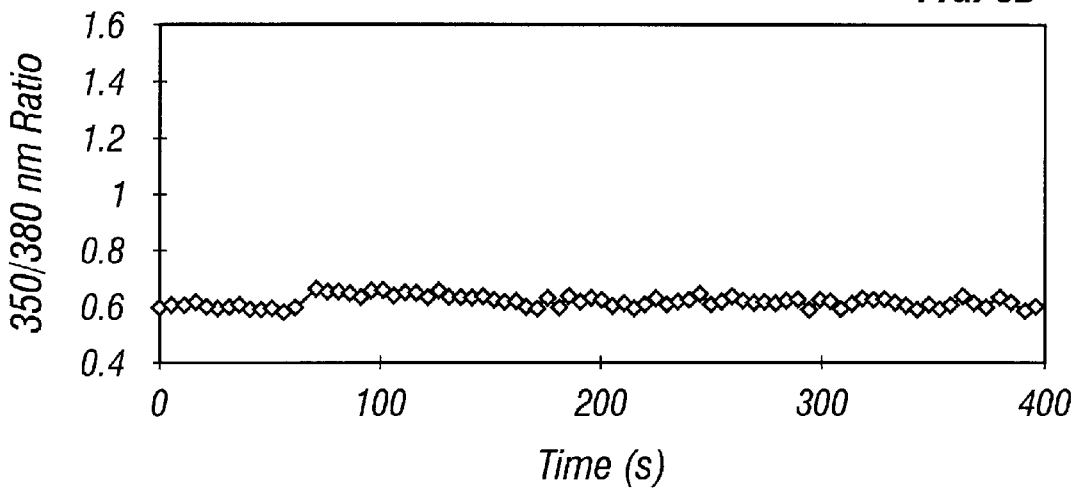
Figure 8C:
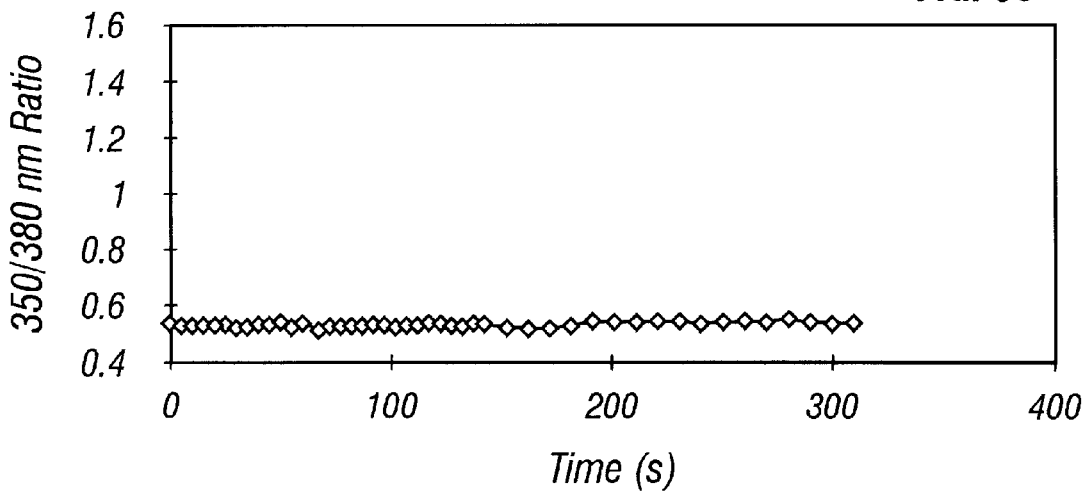

FIGS. 8A–C: shows activation of a Gαs subtype GPCR using promiscuous Gα protein in a cell-based (stably transfected constructs for both the promiscuous Gα-protein and GPCR) calcium indicator assay.

Pane A: Calcium imaging of the Gα15/Gαs-receptor dual stable pool-2. 10 μm agonist was added 40 seconds after the starting of the experiment.

Panel B: Calcium imaging of the Gαs-receptor stable pool-2. 10 μM agonist was added 40 seconds after the starting of the experiment.

Panel C: Clacium imaging of the Gα15 stable pool-H. 10 μM agoinst was added 40 seconds after the starting of the experiment.

DEFINITIONS

Unless defined otherwise, all technical and scientific terms used herein have the same meaning as commonly understood by one of ordinary skill in the art to which this invention belongs. Generally, the nomenclature used herein and the laboratory procedures in spectroscopy, drug discovery, cell culture, and molecular genetics, described below are those well known and commonly employed in the art. Standard techniques are typically used for preparation of signal detection, recombinant nucleic acid methods, polynucleotide synthesis, and microbial culture and transformation (e.g., electroporation, and lipofection). The techniques and procedures are generally performed according to conventional methods in the art and various general references (see generally, Sambrook et al. Molecular Cloning: A Laboratory Manual, 2d ed. (1989) Cold Spring Harbor Laboratory Press, Cold Spring Harbor, N.Y., and Lakowicz, J. R. *Principles of Fluorescence Spectroscopy*, New York: Plenum Press (1983) for fluorescence techniques, which are incorporated herein by reference) which are provided throughout this document. Standard techniques are used for chemical syntheses, chemical analyses, and biological assays. As employed throughout the disclosure, the following terms, unless otherwise indicated, shall be understood to have the following meanings:

"Fluorescent donor moiety" refers to the radical of a fluorogenic compound, which can absorb energy and is capable of transferring the energy to another fluorogenic molecule or part of a compound. Suitable donor fluorogenic molecules include, but are not limited to, coumarins and related dyes xanthene dyes such as fluoresceins, rhodols, and rhodamines, resorufins, cyanine dyes, bimanes, acridines, isoindoles, dansyl dyes, aminophthalic hydrazides such as luminol and isoluminol derivatives, aminophthalimides, aminonaphthalimides, aminobenzofurans, aminoquinolines, dicyanohydroquinones, and europium and terbium complexes and related compounds.

"Quencher" refers to a chromophoric molecule or part of a compound, which is capable of reducing the emission from a fluorescent donor when attached to the donor. Quenching may occur by any of several mechanisms including fluorescence resonance energy transfer, photoinduced electron transfer, paramagnetic enhancement of intersystem crossing, Dexter exchange coupling, and excitation coupling such as the formation of dark complexes.

"Acceptor" refers to a quencher that operates via fluorescence resonance energy transfer. Many acceptors can re-emit the transferred as energy as fluorescence. Examples include coumarins and related fluorophores, xanthenes such as fluoresceins, rhodols, and rhodamines, resorufins, cyanines, difluoroboradiazaindacenes, and phthalocyanines. Other chemical classes of acceptors generally do not re-emit the transferred energy. Examples include indigos, benzoquinones, anthraquinones, azo compounds, nitro compounds, indoanilines, di- and triphenylmethanes.

"Binding pair" refers to two moieties (e.g. chemical or biochemical) that have an affinity for one another. Examples of binding pairs include antigen/antibodies, lectin/avidin, target polynucleotide/probe oligonucleotide, antibody/anti-antibody, receptor/ligand, enzyme/ligand and the like. "One member of a binding pair" refers to one moiety of the pair, such as an antigen or ligand.

"Dye" refers to a molecule or part of a compound that absorbs specific frequencies of light, including but not limited to ultraviolet light. The terms "dye" and "chromophore" are synonymous.

"Fluorophore" refers to a chromophore that fluoresces.

"Membrane-permneant derivative" refers a chemical derivative of a compound that has enhanced membrane permeability compared to an underivativized compound. Examples include ester, ether and carbamate derivatives. These derivatives are made better able to cross cell membranes, i.e. membrane permeant, because hydrophilic groups are masked to provide more hydrophobic derivatives. Also, masking groups are designed to be cleaved from a precursor (e.g., fluorogenic substrate precursor) within the cell to generate the derived substrate intracellularly. Because the substrate is more hydrophilic than the membrane permeant derivative it is now trapped within the cells. "Isolated polynucleotide" refers a polynucleotide of genomic, cDNA, or synthetic origin or some combination there of, which by virtue of its origin the "isolated polynucleotide" (1) is not associated with the cell in which the "isolated polynucleotide" is found in nature, or (2) is operably linked to a polynucleotide which it is not linked to in nature.

"Isolated protein" refers a protein, usually of cDNA, recombinant RNA, or synthetic origin or some combination thereof, which by virtue of its origin the "isolated protein" (1) is not associated with proteins that it is normally found with in nature, (2) is isolated from the cell in which it normally occurs, (3) is isolated free of other proteins from the same cellular source, e.g. free of human proteins, (4) is expressed by a cell from a different species, or (5) does not occur in nature. "Isolated naturally occurring protein" refers to a protein which by virtue of its origin the "isolated naturally occurring protein" (1) is not associated with proteins that it is normally found with in nature, or (2) is isolated from the cell in which it normally occurs or (3) is isolated free of other proteins from the same cellular source, e.g. free of human proteins.

"Polypeptide" as used herein as a generic term to refer to native protein, fragments, or analogs of a polypeptide sequence. Hence, native protein, fragments, and analogs are species of the polypeptide genus. Preferred Gα polypeptides, include those with the polypeptide sequence represented in the SEQUENCE ID LISTING and any other protein having activity similar to such Gα proteins as measured by one or more of the assays described herein. SEQ. ID NO.: 1 is $G\alpha_{16}$ (murine). SEQ. ID NO. 2 is $G\alpha_{15}$ (human). Gα polypeptides or proteins can include any protein having sufficient activity for detection in the assays described herein.

"Naturally-occurring" as used herein, as applied to an object, refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences, such as when the appropriate molecules (e.g., inducers and polymerases) are bound to the control or regulatory sequence(s).

"Control sequence" refers to polynucleotide sequences which are necessary to effect the expression of coding and non-coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, components whose presence can influence expression, and can also include additional components whose presence is advantageous, for example, leader sequences and fusion partner sequences.

"Polynucleotide" refers to a polymeric form of nucleotides of at least 10 bases in length, either ribonucleotides or deoxynucleotides or a modified form of either type of nucleotide. The term includes single and double stranded forms of DNA.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, 1972, Volume 5, National Biomedical Research Foundation, pp. 101–110, and Supplement 2 to this volume, pp. 1–10. The two sequences or parts thereof are more preferably homologous if their amino acids are greater than or equal to 30% identical when optimally aligned using the ALIGN program.

"Corresponds to" refers to a sequence that is homologous (i.e., is identical, not strictly evolutionarily related) to all or a portion of a reference sequence.

The following terms are used to describe the sequence relationships between two or more polynucleotides: "reference sequence," "comparison window," "sequence identity," "percentage of sequence identity," and "substantial identity." A "reference sequence" is a defined sequence used as a basis for a sequence comparison; a reference sequence may be a subset of a larger sequence, for example, as a segment of a fall-length cDNA or gene sequence given in a sequence listing such as a SEQ. ID NO. 1, or may comprise a complete cDNA or gene sequence. Generally, a reference sequence is at least 400 nucleotides in length, frequently at least 600 nucleotides in length, and often at least 800 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 50 percent sequence identity, preferably at least 60 to 70 percent sequence identity, more usually at least 80 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison.

As applied to proteins, the term "substantial identity" means that two protein sequences, when optimally aligned, such as by the programs GAP or BESTFIT using default gap weights, typically share at least 70 percent sequence identity, preferably at least 80 percent sequence identity, more preferably at least 90 percent sequence identity, and most preferably at least 95 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alaninevaline, glutamic-aspartic, and asparagine-glutamine. "Promiscuous Gα protein" refers to a protein with the promiscuous coupling activity of one of the Gα proteins of the SEQ. ID listing. Preferably, the promiscuous Gα protein can couple to at least one GPCR that normally couples to a Gα protein other than a promiscuous Gα protein. Examples of Gα. proteins, include Gαq, Gαs, Gαi and Gα12. Promiscuous Gα protein coupling activity can be measured with an endogenously or heterologously expressed GPCR using the assays described herein. Preferably, a promiscuous Gα protein can couple to at least two different types of GPCRs that normally couple to one of the following Gα proteins, Gαq, Gαs, Gαi and Gα12. More preferably, a promiscuous Gα protein can couple to at least three different types of GPCRs that normally couple to one of the following Gα proteins, Gαq, Gαs, Gαi and Gα12. Promiscuous Gα proteins permit coupling under conditions that would not occur with a Gα protein and a receptor of a different Gα subtype, unless the Gα protein was expressed at sufficiently high levels to promote coupling with a GFCR that is not its normal coupling partner. Examples of $G\alpha_{15}$ include (Wilke, T. M. et al., PNAS, Vol. 88 pp. 10049–10053, 1991) and $G\alpha_{16}$ include (Amatruda, T. T. et al., PNAS, Vol. 88 pp. 5587–5591, 1991). It is understood that promiscuous Gα proteins do not include members of Gαq, Gαs, Gαi and Gα12 proteins that couple to only one type of GPCR "Modulation" refers to the capacity to either enhance or inhibit a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "modulator" refers to a chemical compound (naturally occurring or nonnaturally occurring), such as a biological macromolecule (e.g., nucleic acid, protein, nonpeptide, or organic molecule), or an extract made from biological materials such as bacteria, plants, fungi, or animal (particularly mammalian) cells or tissues. Modulators are evaluated for potential activity as inhibitors or activators (directly or indirectly) of a biological process or processes (e.g., agonist, partial antagonist, partial agonist, inverse agonist, antagonist, antineoplastic agents, cytotoxic agents, inhibitors of neoplastic transformation or cell proliferation, cell proliferation-promoting agents, and the like) by inclusion in screening assays described herein. The activity of a modulator may be known, unknown or partially known.

"Sequence homology" refers to the proportion of base matches between two nucleic acid sequences or the proportion amino acid matches between two amino acid sequences. When sequence homology is expressed as a percentage, e.g., 50%, the percentage denotes the proportion of matches over the length of sequence from a desired sequence (e.g., SEQ. ID NO. 1) that is compared to some other sequence. Gaps (in either of the two sequences) are permitted to maximize matching; gap lengths of 15 bases or less are usually used, 6 bases or less are preferred with 2 bases or less more preferred.

The term "test chemical" refers to a chemical to be tested by one or more screening method(s) of the invention as a putative modulator.

The terms "label" or "labeled" refers to incorporation of a detectable marker, e.g., by incorporation of a radio labeled amino acid or attachment to a polypeptide of biotinyl moieties that can be detected by marked avidin (e.g., streptavidin containing a fluorescent marker or enzymatic activity that can be detected by optical, or calorimetric methods). Various methods of labeling polypeptides and glycoproteins are known in the art and may be used. Examples of labels for polypeptides include, but are not limited to, the following: radioisotopes (e.g., $^{3}H$, $^{14}C$, $^{35}S$, $^{125}I$, $^{131}I$), fluorescent labels (e.g., FITC, rhodamine, lanthanide phosphors), enzymatic labels (or reporter genes) (e.g., horseradish peroxidase, β-galactosidase, β-latamase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

"Fluorescent label" refers to incorporation of a detectable marker, e.g., by incorporation of a fluorescent moiety to a chemical entity that binds to a target or attachment to a polypeptide of biotinyl moieties that can be detected by avidin (e.g., streptavidin containing a fluorescent label or enzymatic activity that can be detected by fluorescence detection methods). Various methods of labeling polypeptides and glycoproteins are known in the art and may be used. Examples of labels for polypeptides include, but are not limited to dyes (e.g., FITC and rhodamine), intrinsically fluorescent proteins, and lanthanide phosphors. In some embodiments, labels are attached by spacer arms of various lengths to reduce potential steric hindrance.

"Reporter gene" refers to a nucleotide sequence encoding a protein that is readily detectable either by its presence or activity, including, but not limited to, luciferase, green fluorescent protein, chloramphenicol acetyl transferase, β-galactosidase, secreted placental alkaline phosphatase, β-lactamase, human growth hormone, and other secreted enzyme reporters. Generally, reporter genes encode a polypeptide not otherwise produced by the host cell, which is detectable by analysis of the cell(s), e.g., by the direct fluorometric, radioisotopic or spectrophotometric analysis of the cell(s) and preferably without the need to kill the cells for signal analysis. Preferably, the gene encodes an enzyme, which produces a change in fluorometric properties of the host cell, which is detectable by qualitative, quantitative or semi-quantitative function of transcriptional activation. Exemplary enzymes include esterases, phosphatases, proteases (tissue plasminogen activator or urokinase) and other enzymes whose function can be detected by appropriate chromogenic or fluorogenic substrates known to those skilled in the art.

"Signal transduction detection system" refers to system for detecting signal transduction across a cell membrane, typically a cell plasma membrane. Such systems typically detect at least one activity or physical property directly or indirectly associated with signal transduction. For example, an activity or physical property directly associated with signal transduction is the activity or physical property of either the receptor (e.g., GPCR),or a coupling protein (e.g., a Gα protein). Signal transduction detection systems for monitoring an activity or physical property directly associated with signal transduction, include GTPase activity, and conformational changes. An activity or physical property indirectly associated with signal transduction is the activity or physical property produced by a molecule other than by either the receptor (e.g., GPCR), or a coupling protein (e.g., a Gα protein) and associated with receptor (e.g., GPCR), or a coupling protein (e.g., a Gα protein). Such indirect activities and properties include changes in intracellular levels of molecules (e.g., ions (e.g., Ca, Na or K), second messenger levels (e.g., cAMP, cGMP and inostol phosphate)), kinase acitvites, transcriptional activity, enzymatic activity, phospholipase activities, ion channel activities and phosphatase activites. Signal transduction detection systems for monitoring an activity or physical property indirectly associated with signal transduction, include transcriptional-based assays, enzymatic assays, intracellular ion assays and second messenger assays.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference).

A DETAILED DESCRIPTION OF THE PREFERRED EMBODIMENTS

The invention provides cells and methods for screening or characterizing G-protein coupled receptors (GPCRs), ligands for GPCRs, and compounds that modulate signal transduction (e.g., agonists and antagonists). The term "G-protein coupled receptor" is used herein in accordance with its conventional definition. Such receptors are cell surface receptors that typically contain seven transmembrane regions and that transduce signals (e.g., sensory, hormonal, and neurotransmitter signals) from extracellular environments to intracellular environments.

Included within the invention are cells that are useful for expressing G proteins and practicing methods of the invention. A preferred cell is a stable, isolated cell that comprises a promiscuous Gα protein construct comprising a promoter operably linked to a gene (or polynucleotide) that encodes a polypeptide with the biological activity of a promiscuous Gα protein. A "stable isolated cell" of the invention is a cell that retains a construct typically longer than at least 3 to 4 passages in tissue culture, preferably longer than 6 to 10 passages and most preferably longer than about 12 passages. An "isolated" cell refers to a cell in an in vitro state (e.g., a cell of a mammalian tissue culture). The cells that are useful in the invention include both eukaryotic and prokaryotic cells that contain the constructs described herein. Preferably, the cell is a cell of a mammalian cell line (e.g., a COS-7 cell); human cells are also preferred (e.g., a human T lymphocyte). Although not preferred, yeast cells can also be used.

A "construct," when used in the context of molecular biology, is any genetically engineered nucleic acid (e.g., a plasmid, restriction fragment or an engineered chromosome). As used herein, a "promoter" is the minimal sequence sufficient to direct transcription of a gene (including a cDNA encoding a protein) in an eukaryote. Preferably, the promoter is derived from an eukaryotic gene or a virus that can direct transcription in an eukaryotic cell. A promoter can include a TATA box, a CAAT box, and a transcriptional start site. The term "gene" refers to a polynucleotide that encodes a protein, such as a cDNA encoding a protein.

Polypeptides that have the biological activity of a Gα protein are those polypeptides that are able to transduce a signal (including extracellular signals) to an effector(s) in a G-protein signaling pathway. Typically, such a polypeptide or protein, in its inactive state, is associated with GDP and the βγ dimer of a G-protein. In its "active" state, the polypeptide typically is associated with GTP and disassociated from the βγ dimer of a G-protein. The unassociated Gα protein is able to transduce a signal to an effector in the G-protein signaling pathway. Examples promiscuous Gα proteins include promiscuous $G\alpha_{16}$ protein and a promiscuous $G\alpha_{15}$ protein. Either promiscuous $G\alpha_{16}$ protein or a promiscuous $G\alpha_{15}$ protein can couple to a GPCR that normally couples to $G_i$, $G_s$ or $G_q$ (see FIG. 1). Preferably, the promiscuous Gα protein employed in the invention has the ability to couple with specificity to an effector in the G-protein signaling pathway. For example, the promiscuous $G\alpha_{16}$ and $G\alpha_{15}$ proteins each retain the ability to specifically activate the β isoformn of phospholipase C.

Preferably, the nucleotide sequence of a promiscuous Gα protein has at least 70% (more preferably, at least 80% or 95%) sequence identity to the nucleotide sequence of $G\alpha_{16}$ (SEQ ID NO: 1) and/or $G\alpha_{15}$ (SEQ ID NO: 2). Other preferred promiscuous Gα proteins are those that are encoded by degenerate variants of the nucleotide sequences of promiscuous $G\alpha_{16}$ (SEQ ID NO: 1) and/or $G\alpha_{15}$ (SEQ ID NO: 2). A "degenerate variant" of a nucleotide sequence is a nucleotide sequence that encodes the same amino acid sequence as a given nucleotide sequence, but in which at least one codon in the nucleotide sequence is different, because two or more different codons can encode the same amino acid. Accordingly, numerous degenerate variants can encode the promiscuous Gα proteins of SEQ ID NO: 3 and SEQ ID NO: 4. Other preferred promiscuous Gα protein are those that are encoded by conservative variations of the nucleotide sequences of $G\alpha_{16}$ (SEQ ID NO: 1) and/or $G\alpha_{15}$ (SEQ ID NO: 2). A "conservative variation" denotes the replacement of an amino acid residue by another, biologically similar, residue. Examples of conservative variations include the substitution of one hydrophobic residue, such as isoleucine, valine, leucine, or methionine, for another, or the substitution of one polar residue for similar polar residue, such as the substitution of arginine for lysine, glutamic acid for aspartic acid, or glutamine for asparagine, and the like.

In some embodiments of the invention it will be desirable to control the level of promiscuous Gα protein expression. High levels of promiscuous Gα protein in a cell can deleteriously alter cell metabolism that can result in cell instability. High levels of promiscuous Gα protein in a cell (or normal Gα protein) can also produce high basal activities GPCRs that results in high background activities, which is not desirable for methods described herein, such as screening chemicals that may modulate receptor activity. Typically, cells having endogenously low levels of normal Gα protein are used. Basal activity levels of GPCRs can be easily tested in a potential cell type to be used for screening with a signal transduction detection system to detect the affect of endogenously expressed G-proteins. Basal activity levels of GPCRs can also be easily tested with either endogenously expressed or heterologously expressed GPCRs in cells expressing a promiscuous Gα protein or other G-proteins.

With GPCRs normally having high basal activity, controlled levels of promiscuous Gα protein can help reduce background activity in a cell while achieving suitable coupling for testing putative modulators of a receptor. The amount promiscuous Gα protein expressed in a cell can be titrated by using, or selecting for, either a weak promoter or an inducible promoter. An inducible promoter offers the advantage, compared to a weak promoter, of regulatable expression of promiscuous Gα protein. By using an inducible promoter the amount inducer can be used to optimize the signal to noise ratio of a screen for GPCR modulators by adjusting the amount of promiscuous Gα protein expression the cell.

An "inducible" promoter is a promoter that, in the absence of an inducer (e.g., doxycyclin) does not direct expression, or directs low levels of expression (e.g., produces less than 500 proteins per cell at steady state) of an operably linked gene (including cDNA). In the presence of an inducer, expression promiscuous Gα protein directed by the inducible promoter is typically increased at least 3-fold (preferably at least 10- 100- or 1,000-fold). Other useful inducible promoters include those that are inducible by IPTG or ecdysone. If desired, an inducible promoter can include a first promoter (e.g., a cytomegalovirus promoter) operably linked to a tet operator to regulate the first promoter (see, Gossen and Bujard, 1992, Proc. Natl. Acad. Sci. 89:5547–5551).

Many embodiments of the invention will include a polynculeotide encoding a GPCR not naturally occurring in the cell and a promiscuous Gα protein construct. The GPCR will typically not be under the control of the control sequence controlling promiscuous Gα protein expression. The GPCR may be a GPCR of known function or of protein of unknown function, such as an orphan GPCR. Promoters known in the art can be used to either constitutively or inducible express the receptor or putative receptor.

If desired, a cell of the invention can contain a polynucleotide having a control sequence and encoding a protein useful in signal transduction detection system. The construct is designed to detect activation of a Gα protein. This second construct is typically located on a second vector. It can include a reporter gene that is operably linked to a promoter that is modulated (directly or indirectly) by an active promiscuous Gα protein. Preferably, the expression of the reporter gene can be detected by detecting a change in fluorescence emission of a sample that contains the cell.

For instance, the reporter system described in PCT publication WO96/30540 (Tsien) has significant advantages over existing reporters for gene integration analysis, as it allows sensitive detection and isolation of both expressing and non-expressing single living cells. This assay system uses a non-toxic, non-polar fluorescent substrate, which is easily loaded and then trapped intracellularly. Cleavage of the fluorescent substrate by β-lactamase yields a fluorescent emission shift as substrate is converted to product. Because the β-lactamase reporter readout can be ratiometric, it is unique among reporter gene assays in that it controls variables such as the amount of substrate loaded into individual cells. The stable, easily detected, intracellular readout simplifies assay procedures by eliminating the need for washing steps, which facilitates screening with cells using the invention. Preferably, a ratiometric fluorescent signal transduction detection system can be used with the invention. Preferred fluorogenic substrates are described in the Examples.

Other reporter genes such as polynucleotides encoding a polypeptide having the biological activity of green fluorescent protein (GFP) can be used.

A promoter is considered to be "modulated" by an active, promiscuous Gα protein when the expression of a reporter gene to which the promoter is operably linked is either increased or decreased upon activation of the promiscuous Gα protein. It is not necessary that the active, promiscuous Gα protein directly modulate reporter gene expression.

For example, embodiments of the invention presume that activation of $G\alpha_{15}$ or $G\alpha_{16}$ can, through a G-protein signaling pathway, activate PLCβ, which in turn increases intracellular calcium levels. An increase in calcium levels can lead to modulation of a "calcium-responsive" promoter that is part of a signal transduction detection system, i.e., a promoter that is activated (e.g., a NFAT promoter) or inhibited by a change in calcium levels. One example of an NFAT DNA binding site is found in Shaw, et al. Science291:202–205 1988. Likewise, a promoter that is responsive to changes in protein kinase C levels (i.e., a "protein kinase C-responsive promoter") can be modulated by an active Gα protein through G-protein signaling pathway. The cells described above can also include a G-protein coupled receptor. Genes encoding numerous GPCRs have been cloned (Simon et al., 1991, Science 252:802–808), and conventional molecular biology techniques can be used to express a GPCR on the surface of a cell of the invention. Preferably, the sum responsive promoter allows only a relatively short lag (e.g., less than 90 minutes) between engagement of the GPCR and transcriptional activation. A preferred responsive promoter includes the nuclear factor of activated T-cell promoter (Flanagan et al., 1991, Nature 352:803–807).

Many cells can be used in the invention, particularly for heterologous expression of a GPCR. Such cells include, but are not limited to; baby hamster kidney (BHK) cells (ATCC No. CCL10), mouse L cells (ATCC No. CCLI.3), Jurkats (ATCC No. TIB 152) and 153 DG44 cells [see, Chasin (1986) Cell. Molec. Genet. 12: 555] human embryonic kidney (HEK) cells (ATCC No. CRL1573), Chinese hamster ovary (CHO) cells (ATCC Nos. CRL9618, CCL61, CRL9096), PC12 cells (ATCC No. CRL17.21) and COS-7 cells (ATCC No. CRL1651). Preferred cells for heterologous cell surface protein expression are those that can be readily and efficiently transfected. Preferred cells include Jurkat cells CHO cells and HEK 293 cells, such as those described in U.S. Pat. No. 5,024,939 and by Stillman et al. (1985) Mol. Cell. Biol. 5: 2051–2060.

GPCRs that can be used with the invention include, but are not limited to, muscarinic receptors, e.g., human M2 (GenBank accession#M16404); rat M3 (GenBank accession#M16407); human M4 (GenBank accession#M16405); human M5 (Bonner, et al., (1988) Neuron 1, pp. 403–410); and the like; neuronal nicotinic acetylcholine receptors, e.g., the human $\alpha_2$, $\alpha_3$, and $\beta_2$, subtypes disclosed in U.S. Ser. No. 504,455 (filed Apr. 3, 1990, which is hereby expressly incorporated by reference herein in its entirety); the human $\alpha_5$ subtype (Chini, et al. (1992) Proc. Natl. Acad. Sci. U.S.A. 89: 1572–1576), the rat $\alpha_2$ subunit (Wada, et al. (1988) Science 240, pp. 330–334); the rat $\alpha_3$ subunit (Boulter, et al. (1986) Nature 319, pp. 368–374); the rat $\alpha_4$ subunit (Goldman, et al. (1987) Cell 48, pp. 965–973); the rat $\alpha_5$ subunit (Boulter, et al. (1990) I. Biol. Chem. 265, pp. 4472–4482); the chicken $\alpha_7$ subunit (Couturier et al. (1990) Neuron 5: 847–856); the rat $\beta_2$ subunit (Deneris, et al. (1988) Neuron 1, pp. 45–54) the rat $\beta_3$ subunit (Deneris, et al. (1989) J. Biol. Chem. 264, pp. 6268–6272); the rat $\beta_4$ subunit (Duvoisin, et al. (1989) Neuron 3, pp. 487–496); combinations of the rat α subunits, and s β subunits and a and p subunits; GABA receptors, e.g., the bovine x, and $\beta_1$, subunits (Schofield, et al. (1987) Nature 328, pp. 221–227); the bovine $X_2$, and $X_3$, subunits (Levitan, et al. (1988) Nature 335, pp. 76–79); the γ-subunit (Pritchett, et al. (1989) Nature 338, pp. 582–585); the $\beta_2$, and $\beta_3$, subunits (Ymer, et al. (1989) EMBO J. 8, pp. 1665–1670); the δ subunit (Shivers, B.D. (1989) Neuron 3, pp. 327–337); and the like; glutamate receptors, e.g., rat GluR1 receptor (Hollman, et al. (1989) Nature 342, pp. 643–648); rat GluR2 and GluR3 receptors (Boulter et al. (1990) Science 249:1033–1037; rat GluR4 receptor (Keinanen et al. (1990) Science 249: 556–560); rat GluR5 receptor (Bettler et al. (1990) Neuron 5: 583–595); rat GluR6 receptor (Egebjerg et al. (1991) Nature 351: 745–748); rat GluR7 receptor (Bettler et al. (1992) neuron 8:257–265); rat NMDAR1 receptor (Moriyoshi et al. (1991) Nature 354:31–37 and Sugihara et al. (1992) Biochem. Biophys. Res. Comm. 185:826–832); mouse NMDA el receptor (Meguro et al. (1992) Nature 357: 70–74); rat NMDAR2A, NMDAR2B and NMDAR2C receptors (Monyer et al. (1992) Science 256: 1217–1221); rat metabotropic mGluR1 receptor (Houamed et al. (1991) Science 252: 1318–1321); rat metabotropic mGluR2, mGluR3 and mGluR4 receptors (Tanabe et al. (1992) Neuron 8:169–179); rat metabotropic mGluR5 receptor (Abe et al. (1992) I. Biol. Chem. 267: 13361–13368); and the like; adrenergic receptors, e.g., human β1 (Frielle, et al. (1987) Proc. Natl. Acad. Sci. 84, pp. 7920–7924); human $\alpha_2$ (Kobilka, et al. (1987) Science 238, pp. 650–656); hamster $\beta_2$ (Dixon, et al. (1986) Nature 321, pp. 75–79); and the like; dopamine receptors, e.g., human D2 (Stormann, et al. (1990) Molec. Pharm. 37, pp. 1–6); mammalian dopamine D2 receptor (U.S. Pat. No. 5,128,254); rat (Bunzow, et al. (1988) Nature 336, pp. 783–787); and the like; and the like; serotonin receptors, e.g., human 5HT1a (Kobilka, et al. (1987) Nature 329, pp. 75–79); serotonin 5HT1C receptor (U.S. Pat. No. 4,985,352); human 5HT1D (U.S. Pat. No. 5,155,218); rat 5HT2 (Julius, et al. (1990) PNAS 87, pp.928–932); rat 5HT1c (Julius, et al. (1988) Science 241, pp. 558–564), and the like.

If desired (e.g., for commercial purposes), a cell(s) of the invention can packaged into a container that is packaged within a kit. Such a kit may also contain any of the various isolated nucleic acids, antibodies, proteins, signal transduction detection systems, substrates, and/or drugs described herein, known in the art or developed in the future. A typical kit also includes a set of instructions for any or all of the methods described herein.

METHODS OF THE INVENTION

The invention provides several methods for cloning or characterizing GPCRs, screening or characterizing ligands (e.g., known ligands) of GPCRs, and identifying or characterizing compounds that modulate signal transduction. For example, the invention provides a method for determining whether a "target" polypeptide is a GPCR for a given ligand. The method involves expressing a target polypeptide in a cell described herein that comprises a reporter gene construct (e.g., a construct encoding a β-lactamase reporter gene operably linked to a NFAT promoter). In this method, the test polypeptide is contacted with a chosen ligand, usually of established activity, and a change in reporter gene expression is detected. A "target" polypeptide, which is usually a GPCR, is any polypeptide expressed by a cell that can be assayed for activity using the present invention.

Similar methods can be used to test ligands and compounds using GPCRs of known, partially known and unknown function. A test ligand is a molecule that can be assayed for its ability to bind to a GPCR. A test compound is a molecule that can be assayed for its ability to modulator of signal transduction. Often, such a target polypeptide, test ligand, or test compound is, because of its sequence or structure, suspected of being able to function in a given capacity. Nonetheless, randomly chosen target polypeptides, test ligands, and test compounds also can be used in the methods described herein, and with techniques known in the art or developed in the future. For example, expression of target polypeptides from nucleic acid libraries, can be used to identify proteins involved in signal transduction, such as orphan GPCRs. For instance, this technique can be used to identify physiologically responsive receptors (e.g., taste-responsive GPCRs) where the ligand responsible for inducing a physiological event is known (e.g., a given taste sensation is known).

The invention also includes enhancement of reporter gene expression in a signal transduction detection system. This particularly useful for improving the signal to noise ratio in a screening assay. It generally involves contacting the cell with a molecule ("subthreshold regulating molecule") that alters the activity of a cellular process to a level subthreshold to the activation of a cellularly responsive control sequence that is operably linked to the reporter gene. Because the level of cellular activity is subthreshold, the reporter gene has a low expression level. The reporter gene system, however, is poised for activation by a change in cellular process induced by either a test chemical, test ligand or expression of target protein. Such cellularly responsive control sequences can be responsive elements known in the art in other applications. Such response elements, however, do not need be responsive to their naturally occurring signal, since the assay may occur in cells lacking the required constituents for activation by a naturally occurring signal. The subthreshold regulating molecule can either increase or decrease the activity of the cellular process. It is understood that the cellular process may not only be "classic" cellular process, such as an enzymatic activity, but it also includes levels of cellular entities (e.g., ions, metabolites and second messengers) or other measurable properties of the cell (e.g., cell volume, chromatin density, etc.). Cells described herein are preferred for this method. Other cells, however, can be used as well which express Gα proteins endogenously, or heterologously.

For example, in order to enhance detection of expression of a reporter gene, the cell can be contacted with a compound (e.g., a calcium ionophore) that increases calcium levels inside of the cell. By increasing calcium levels inside the cell, the probability that activation of a G-protein will activate expression of a reporter gene is greatly enhanced. Preferably, the calcium levels are increased to a level that is just below the threshold level for activation of a calcium-responsive promoter, such as an NFAT promoter (see FIG. 2). In practice, ionomycin typically is added at a concentration of about 0.01 to 3 $\mu$M, preferably 0.03 $\mu$M. Cells described herein are preferred for this method. Other cells, however, can be used as well which express Gα proteins endogenously, or heterologously.

In an alternate method of enhancing a signal transduction detection system, thapsigargin is added to the cell to set intracellular calcium levels at subthreshold levels to enhance reporter gene activation. Thapsigargin is added to the cell at a concentration of about 1 to 50 nM, with the effect of partially depleting intracellular calcium pools and slowing the re-filling of such pools (Thastrup et al., 1990, Proc. Natl. Acad. Sci. 87:2466–2470). If desired, thapsigargin can be used at a higher concentration (e.g., 200 nM to 1 $\mu$M) in a "$Ca^{+2}$-clamp" protocol, in which membrane potential is used to set the baseline calcium concentration (Negulescu et al., 1994, Proc. Natl. Acad. Sci. 91:2873–2877). This can be applied to screening for modulators of signal transduction using a reporter gene system with a calcium-responsive promoter. Cells described herein are preferred for this method. Other cells, however, can be used as well which express Gα proteins endogenously, or heterologously.

In yet another method of the invention, conventional molecular biology techniques can be used to express a calcium modulating ligand in cells, and thereby increase calcium levels (Bram et al., 1994, Nature 371:355–358). This can be applied to screening for modulators of signal transduction using a reporter gene system with a calcium-responsive promoter. Cells described herein are preferred for this method. Other cells, however, can be used as well which express Gα proteins endogenously, or heterologously.

A related method of the invention for enhancing detection of expression of the reporter gene involves contacting the cell with an activator of protein kinase C. Typically, this method involves contacting the cell with 1 to 3 nM of phorbol myristate acetate (PMA) or another phorbol ester; preferably PMA is used at a concentration of 0.3 nM. The PMA concentration can be titrated to achieve sub threshold levels. Various analogs of PMA that retain this activity are known in the art, and can be used in the invention. Cells described herein are preferred for this method. Other cells, however, can be used as well which express Gα proteins endogenously, or heterologously.

The invention also provides a method for determining whether a "test" ligand is a ligand for a given GPCR. In this method, a selected GPCR is expressed in a cell, such as a cell of the invention, which contains a construct and encodes a reporter gene. The cell is contacted with a test ligand, and a change in expression of the reporter gene is detected. This method is particularly well suited for identifying a ligand not known to bind to the receptor and it can also be used to determine receptor selectivity. In this method, the change in expression of the reporter gene can be compared for a sample of cells in the presence, versus in the absence, of the test ligand in order to identify ligand specific activation. Cells described herein are preferred for this method. Other cells, however, can be used as well which express Gα proteins endogenously, or heterologously.

The aforementioned methods can readily be adapted to provide a method for characterizing the ability of a ligand to interact with a panel of GPCRs of interest. In such an assay, the first GPCR of interest is expressed in a cell, such as a cell of the invention, that contains a construct encoding a reporter gene. In a second cell (in a second, separate sample), a second GPCR of interest is expressed along with reporter gene system. Additional GPCRs can be expressed in additional cells with reporter gene systems. Typically, these cells differ only with respect to the GPCR that is expressed. Each sample of cells is contacted with the "test" ligand of interest, and a change in reporter gene expression is detected for each cell sample. By comparing the changes in expression of the reporter gene between cell samples, one can characterize the functional activity of the ligand. This method is particularly well suited for assaying the ability of a known ligand to interact with several GPCRs that are known to be related. Thus the selectivity of the ligand can be determined. For example, various muscarinic receptors (e.g., $M_1$, $M_2$, and $M_3$) can be expressed, separately, on a cell. If desired, various modulators of G-protein activity (e.g., agonists and antagonists) can be characterized in a variation of this method. Cells described herein are preferred for this method. Other cells, however, can be used as well which express Gα proteins endogenously, or heterologously.

The invention also provides a general method for determining whether a test compound modulates signal transduction in a cell. This method also employs a cell, such as a cell of the invention, that includes a construct, and that expresses a reporter gene. In this method, the cell expresses a GPCR, and the cell is contacted with a ligand that, in the absence of a test compound, activates signal transduction. The cell is also contacted with a test compound, and a change in expression of the reporter gene indicates that the test compound modulates signal transduction in the cell.

In a variation of this method, the invention provides a "receptor-less" method for determining whether a test compound modulates signal transduction. In this variation, the cell is not engineered to express a GPCR. In lieu of contacting the cell with a ligand, the cell is contacted with a compound that directly activates a Gα protein encoded by a construct within the cell. Examples of such compounds include mastoparan (Calbiochem) and aluminum fluoride. These compounds typically are used at concentrations of 0.5 to 5 mM. A change in expression of a reporter gene indicates that the test compound modulates signal transduction in the cell. Such a change also indicates that the compound affects signaling events that occur subsequent to receptor signaling in the signaling pathway.

The invention also provides a method for determining whether a test polypeptide is a GPCR for a given ligand, without employing a second genetic construct expressing a reporter gene. In this method, a test polypeptide is expressed in a stable, isolated cell that carries a genetic construct that includes a promoter operably linked to a gene that encodes a polypeptide having the biological activity of a promiscuous Gα protein. The test polypeptide is contacted with a ligand, and an increase in calcium levels within the cell is detected. Any of the art-known methods for detecting a change in calcium levels can be used in this method (Negulescu and Machen, 1990, Meth. in Enzymol. 192:38–81). In a preferred method, the increase is detected by contacting the cell with fura-2 (available from Molecular Probes; Eugene, OR) and detecting a change in fluorescence emission of a sample that includes the cell.

The invention offers several advantages. By employing promiscuous G-proteins, the invention allows the use of a single intracellular signaling pathway (e.g., activation of PLCβ) to analyze GPCRs that normally couple specifically to G-proteins of a single family. By providing methods that employ living cells, the invention allows a receptor or ligand that is identified in an assay to be cloned. By employing fluorescent detection methods, the invention, in various embodiments, allows a practitioner to characterize a single cell. Accordingly, convenient cell-sorting methods, such as FACS, can be used to analyze and isolate cells. The fluorescent assays employed in the invention also provide a stable, non-labile indicator of G-protein activation. Such a stable signal (lasting up to twelve hours) allows a practitioner to analyze numerous samples in parallel, thus rendering the invention useful for high throughput screening of "test" polypeptides, ligands, and compounds. The invention provides, for the first time, an assay for associating occupancy of any GPCR with gene expression, as detected by a fluorescence emission. In addition, by providing methods for enhancing detection of G-protein activation, the invention provides a sensitive assay for detecting low levels, or brief activation, of a G-protein.

The kits can be produced to accomplish the methods described herein. Such kits can include the polynucleotides for GPCR expression, cells for GPCR expression or Gα protein expression and signal transduction detection systems, such reporter gene systems.

EXAMPLES

The following examples are intended to illustrate but not limit the invention. While they are typical of those methods that might be used, other procedures known to those skilled in the are may alternatively be used.

Example 1—Synthesis of a β Lactamase substrate (compound 7b)

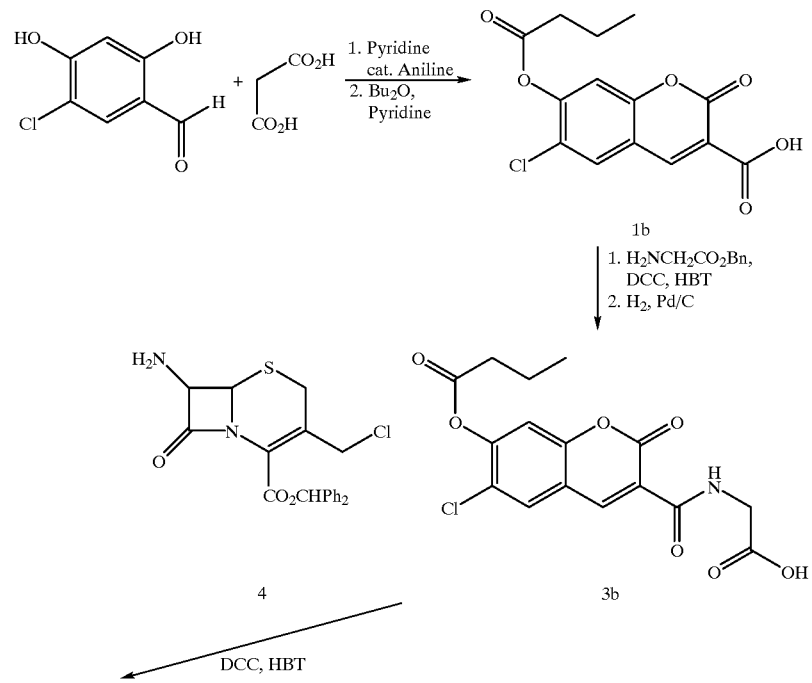

-continued

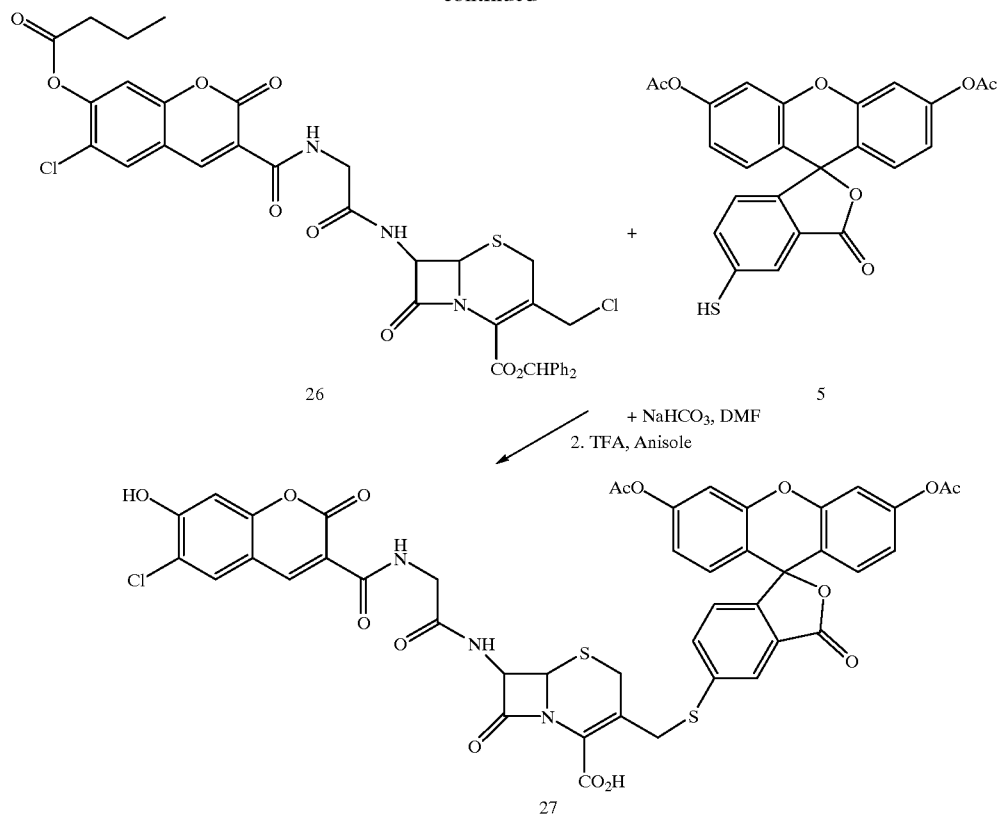

For synthesis of 2,4 dihydroxy-5-chlorobenzaldehyde, 21.7 g (0.15 Mol) 4-chlororesorcinol were dissolved in 150 ml dry diethyl ether and 27 g finely powdered zinc (II) cyanide and 0.5 g potassium chloride were added with stirring. The suspension was cooled on ice. A strong stream of hydrogen chloride gas was blown into the solution with vigorous stirring. After approximately 30 minutes the reactants were dissolved. The addition of hydrogen chloride gas was continued until it stopped being absorbed in the ether solution (approx. 1 hour). During this time a precipitate formed. The suspension was stirred for one additional hour on ice. Then the solid was let to settle. The ethereal solution was poured from the solid. The solid was treated with 100 g of ice and heated to 100° C. in a water bath. Upon cooling the product crystallized in shiny plates from the solution. They were removed by filtration on dried over potassium hydroxide. The yield was 15.9 g (0.092 Mol, 61%). $^1$H NMR (CDCl$_3$): δ6.23 ppm (s, 1H, phenol), δ6.62 ppm (s, 1H, phenyl), δ7.52 ppm (s, 1H, phenyl), δ9.69 ppm (s, 1H, formyl), δ11.25 ppm (s, 1H, phenol).

To prepare 3-carboxy 6-chloro 7-hydroxy coumarin, 5.76 g (0.033 Mol) 2,4-dihydroxy-5-chlorobenzaldehyde and 7.2 g (0.069 Mol) malonic acid were dissolved in 5 ml warm pyridine. 75 μl Aniline were stirred into the solution and the reaction let to stand at room temperature for 3 days. The yellow solid that formed was broken into smaller pieces and 50 ml ethanol was added. The creamy suspension was filtered through a glass frit and the solid was washed three times with 1 N hydrochloric acid and then with water. Then the solid was stirred with 100 ml ethyl acetate, 150 ml ethanol and 10 ml half concentrated hydrochloric acid. The solvent volume was reduced in vacuo and the precipitate recovered by filtration, washed with diethyl ether and dried over phosphorous pentoxide. 4.97 g (0.021 Mol, 63%) of product was obtained as a white powder. $^1$H NMR (dDMSO): δ6.95 ppm (s, 1H), δ8.02 ppm (s, 1H), δ8.67 ppm (s, 1H).

To prepare 7-butyryloxy-3-carboxy-6-chlorocoumarin, 3.1 g (12.9 mMol) 3-carboxy-6-chloro-7-hydroxycoumarin were dissolved in 100 ml dioxane and treated with 5 ml butyric anhydride, 8 ml pyridine and 20 mg dimethyl aminopyridine at room temperature for two hours. The reaction solution was added with stirring to 300 ml heptane upon which a white precipitate formed. It was recovered by filtration and dissolved in 150 ml ethyl acetate. Undissolved material was removed by filtration and the filtrate extracted twice with 50 ml 1 N hydrochloric acid/brine (1: 1) and then brine. The solution was dried over anhydrous sodium sulfate. Evaporation in vacuo yielded 2.63 g (8.47 mMol, 66%) of product. $^1$H NMR (CDCl$_3$): δ1.08 ppm (t, 3H, J=7.4 Hz, butyric methyl), δ1.85 ppm (m, 2H, J$_1$δJ$_2$=7.4 Hz, butyric methylene), δ2.68 ppm (t, 2H, J=7.4 Hz, butyric methylene), δ7.37 ppm (s, 1H, coumarin), δ7.84 ppm (s, 1H, coumarin), δ8.86 ppm (s, 1H, coumarin).

Preparation of 7-butyryloxy-3-benzyloxycarbonylmethylaminocarbonyl-6-chlorocoumarin is effected as follows. 2.5 g (8.06 mMol) 7-Butyryloxy-3-carboxy-6-chlorocoumarin, 2.36 g hydroxybenztriazole hydrate (16 mMol) and 1.67 g (8.1 mMol) dicyclohexyl carbodiimide were dissolved in 30 ml dioxane. A toluene solution of O-benzylglycine [prepared by extraction of 3.4 g (10 mMol) benzylglycine tosyl salt with ethyl acetate—toluene—saturated aqueous bicarbonate—water (1:1:1: 1, 250 ml), drying of the organic phase with anhydrous sodium sulfate and reduction of the solvent volume to 5 ml] was added drop wise to the coumarin solution. The reaction was kept at room temperature for 20 hours after which the precipitate was removed by filtration and washed extensively with ethylacetate and acetone. The combined solvent fractions were reduced to 50 ml on the rotatory evaporator upon which one volume of toluene was added and the volume further reduced to 30 ml. The precipitating product was recovered by filtration and dissolved in 200 ml chloroform—absolute ethanol (1:1). The solution was reduced to 50 ml on the rotatory evaporator and the product filtered off and dried in vacuo yielding 1.29 g of the title product. Further reduction of the solvent volume yielded a second crop (0.64 g). Total yield: 1.93 g (4.22 mMol, 52%). $^1$H NMR (CDCl$_3$): δ1.08 ppm (t, 3H, J=7.4 Hz, butyric methyl), δ1.84 ppm (m, 2H, J$_1$δJ$_2$=7.4 Hz, butyric methylene), δ2.66 ppm (t, 2H, J 7.4 Hz, butyric methylene), δ4.29 ppm (d, 2H, J 5.5 Hz, glycine methylene), δ5.24 ppm (s, 2H, benzyl), δ7.36 ppm (s, 1H, coumarin), δ7.38 ppm (s, 5H, phenyl), δ7.77 ppm (s, 1H, coumarin), δ8.83 ppm (s, 1H, coumarin), δ9.15 ppm (t, 1H, J 5.5 Hz, amide).

7-Butyryloxy-3-carboxymethylaminocarbonyl-6-chlorocoumarin was prepared as follows. 920 mg (2 mMol) 7-butyryloxy-3-benzyloxycarbonylmethylamino-carbonyl-6-chlorocoumarin were dissolved in 50 ml dioxane. 100 mg Palladium on carbon (10%) and 100 μl acetic acid were added to the solution and the suspension stirred vigorously in a hydrogen atmosphere at ambient pressure. After the uptake of hydrogen seized the suspension was filtered. The product containing carbon was extracted five times with 25 ml boiling dioxane. The combined dioxane solutions were let to cool upon which the product precipitated as a white powder. Reduction of the solvent to 20 ml precipitates more product. The remaining dioxane solution is heated to boiling and heptane is added until the solution becomes cloudy. The weights of the dried powders were 245 mg, 389 mg and 58 mg, totaling 692 mg (1.88 mMol, 94%) of white product. $^1$H NMR (dDMSO): δ1.02 ppm (t, 3H, J 7.4 Hz, butyric methyl), δ1.73 ppm (m, 2H, J$_1$δJ$_2$=7.3 Hz, butyric methylene), δ2.70 ppm (t, 2H, J 0.67 ppm (s, 1H, coumarin), δ8.35 ppm (s, 1H, coumarin), δ8.90 ppm (s, 1H, coumarin), δ9.00 ppm (t, 1H, J=5.6 Hz, amide).

Coupling of 7-Butyryloxy-3-carboxymethylaminocarbonyl-6-chlorocoumarin with 7-amino-3'-chlorocephalosporanic acid benzhydryl ester was effected as follows. 368 mg (1 mMol) 7-Butyryloxy-3-carboxymethylaminocarbonyl-6-chlorocoumarin, 270 mg hydroxybenztriazole hydrate and 415 mg (1 mMol) 7-amino-3'-chloro cephalosporanic acid benzhydryl ester were suspended in 40 ml dioxane-acetonitrile (1:1). 260 mg (1.25 mMol) dicyclohexylcarbodiimide in 5 ml acetonitrile were added and the suspension was stirred vigorously for 36 hours. The precipitate was removed by filtration and the volume of the solution reduced to 20 ml on the rotatory evaporator. 50 ml Toluene was added and the volume reduced to 30 ml. With stirring 50 ml heptane was added and the suspension chilled on ice. The precipitate was recovered by filtration. It was redissolved in 10 ml chloroform and the remaining undissolved solids were filtered off. Addition of 2 volumes of heptane precipitated the title product which was collected and dried in vacuo and yielded 468 mg (0.64 mMol, 64%) off-white powder. $^1$H NMR (CDCl$_3$): δ1.08 ppm (t, 3H, J 7.4 Hz, butyric methyl), δ1.84 ppm (m, 2H, J$_1$δJ$_2$ 7.4 Hz, butyric methylene), δ2.66 ppm (t, 2H, J 7.4 Hz, butyric methylene), δ3.54 ppm (2d, 2H, J 18.3 Hz, cephalosporin C-2), δ4.24 ppm (2d, 2H, J 5.8 Hz, cephalosporin 3 methylene), δ4.37 ppm (d, 2H, J 3.8 Hz, glycine methylene), δ5.02 ppm (d, 1H, J 4.9 Hz, cephalosporin C-6), δ5.89 ppm (dd, 1H, J$_1$ 9.0 Hz, J$_2$ 5.0 Hz, cephalosporin C-7), δ6.96 ppm (s, 1H, benzhydryl), δ7.30–7.45 ppm (m, 12H, phenyl, coumarin, amide), δ7.79 ppm (s, 1H, coumarin), δ8.84 ppm (s, 1H, coumarin), δ9.28 ppm (t, 1H, J 3.7 Hz, amide).

Coupling of the above product with 5-fluoresceinthiol was effected as follows. 90 mg (0.2 mMol) 5-mercaptofluorescein diacetate disulfide dimer were dissolved in 10 ml chloroform and treated with 25 μl tributyl phosphine and 25 μl water in an argon atmosphere. The solution was kept for 2 hours at ambient temperature and was then added to a solution of 20 mg sodium bicarbonate, 25 mg sodium iodide and 110 mg (0.15 mMol) of the above compound in 10 ml dimethylformamide. After 4 hours the solvents were removed in vacuo and the residue triturated with diethylether. The solid was dissolved in ethyl acetate-acetonitrile (1:1). After removal of the solvents the residue was triturated once more with diethylether yielding 157 mg (0.13 mMol, 88%) of a cream-colored powder product.

A sample of the above compound was treated with a large access of trifluoroacetic acid-anisole (1:1) at room temperature for 20 minutes. The reagents are removed in vacuo and the residue triturated with ether. High performance liquid chromatography of the solid in 45% aqueous acetonitrile containing 0.5% acetic acid gives a product in which the butyrate and the diphenylmethyl esters have been cleaved. It was purified by high performance liquid chromatography on a reverse phase C$_{18}$-column using 45% aqueous acetonitrile containing 5% acetic acid as the eluent.

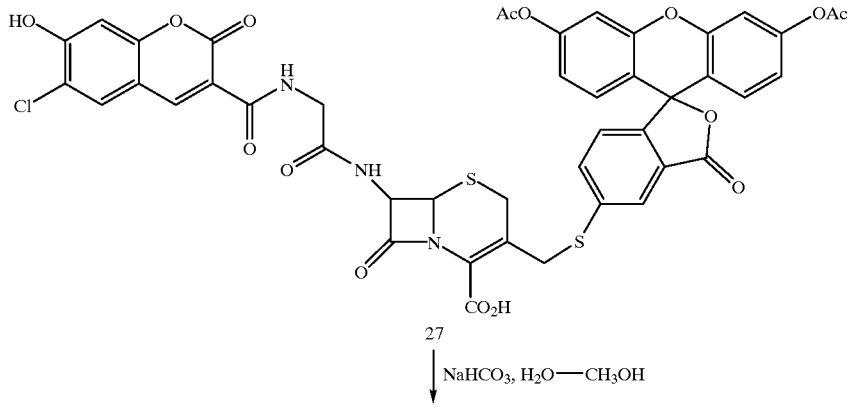

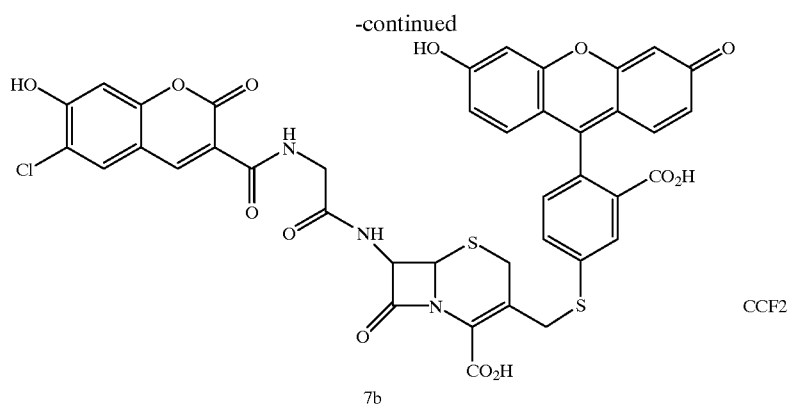

CCF2

Deprotection of the fluorescein acetates in compound 27 was accomplished with sodium bicarbonate in methanol (room temperature, 30 minutes) to provide the fluorescent enzyme substrate CCF2. It was purified by high performance liquid chromatography on a reverse phase $C_{18}$-column using 35% aqueous acetonitrile containing 0.5% acetic acid as the eluent.

derivative of the substrate (CCF2/ac$_2$AM$_2$). It was purified by high performance liquid chromatography on a reverse phase $C_{18}$-column using 65% aqueous acetonitrile containing 0.5% acetic acid as the eluent. CCF2/ac$_2$AM$_2$ is readily converted to CCF2 in the cells'cytoplasm.

The donor and acceptor dyes in substrate CCF2 do not stack. The substrate is fully fluorescent in phosphate buffer

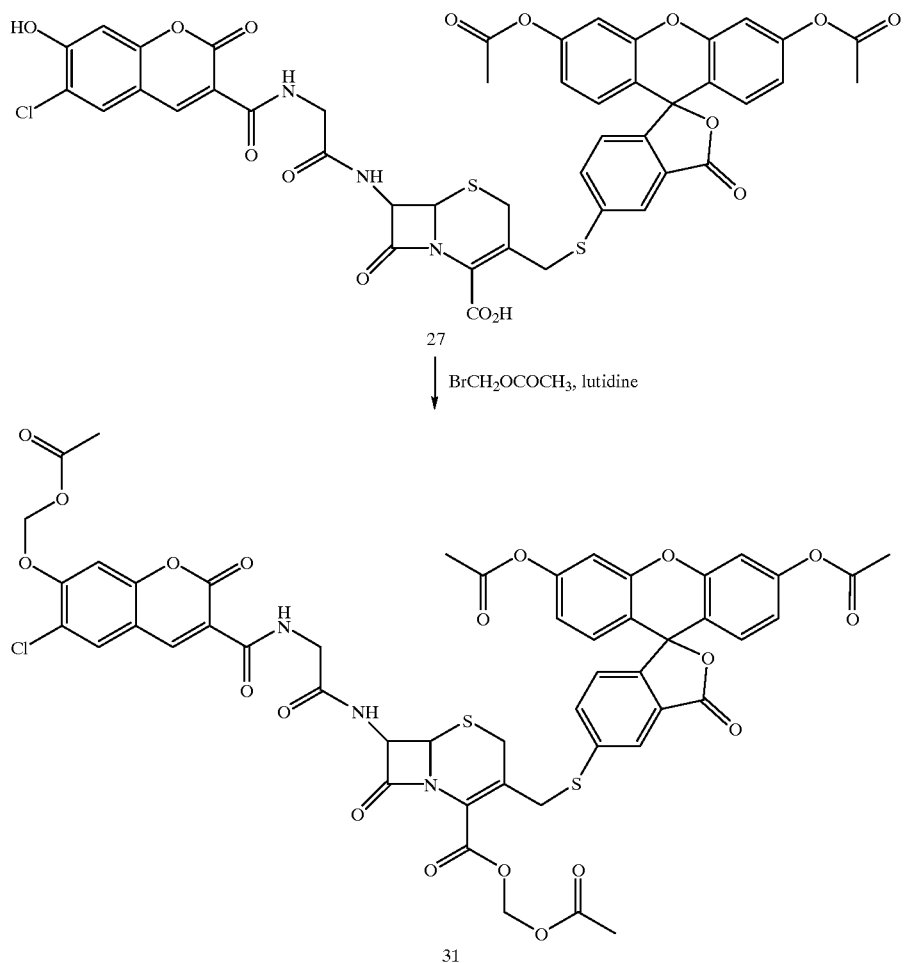

Stirring of compound 27 with excess acetoxymethyl bromide in dry lutidine produced the membrane permeable and there is no formation of the "dark complex" (i.e., addition of methanol does not change the fluorescence spectrum of CCF2, except for the effect of dilution). This is due to the much smaller and more polar nature of the 7-hydroxycoumarin compared to that of the xanthene dyes (eosin, rhodamine, rhodol and resorufin).

The emission spectrum of compound CCF2 in 50 mmolar phosphate buffer pH 7.0 before and after β-lactamase cleavage of the β-lactam ring. In the intact substrate, efficient energy transfer occurs from the 7-hydroxycoumarin moiety to the fluorescein moiety. Excitation of the substrate at 405 nm results in fluorescence emission at 515 nm (green) from the acceptor dye fluorescein. The energy transfer is disrupted when β-lactamase cleaves the β-lactam ring, thereby severing the link between the two dyes. Excitation of the products at 405 nm now results entirely in donor fluorescence emission at 448 nm (blue). The fluorescence emission from the donor moiety increases 25 fold upon β-lactam cleavage. The fluorescence at 515 nm is reduced by 3.5-fold, all of the remaining fluorescence originating from the 7-hydroxycoumarin as its emission spectrum extends into the green. Twenty-five-fold quenching of the donor in the substrate is equivalent to an efficiency of fluorescence energy transfer of 96%. This large fluorescence change upon β-lactam cleavage can readily be used to detect β-lactamase in the cytoplasm of living mammalian cells.

The 7-hydroxycoumarin moiety in the cephalosporin was determined to have a fluorescence quantum efficiency in the absence of the acceptor of 98–100%. This value was determined by comparing the integral of the corrected fluorescence emission spectrum of the dye with that of a solution of 9-aminoacridine hydrochloride in water matched for absorbance at the excitation wavelength. It follows that 7-hydroxycoumarin is an ideal donor dye, as virtually every photon absorbed by the dye undergoes fluorescence energy transfer to the acceptor.

Example 2—Use of a β Lactamase Substrate

Cells of the T-cell lymphoma line Jurkat were suspended in an isotonic saline solution (Hank's balanced salt solution) containing approximately $10^{12}$ β-lactamase enzyme molecules per milliliter (approximately 1.7 nM; Penicillinase 205 TEM R$^+$, from Sigma) and 1 mg/ml rhodamine conjugated to dextran (40 kd) as a marker of loading. The suspension was passed through a syringe needle (30 gauge) four times. This causes transient, survivable disruptions of the cells' plasma membrane and allows entry of labeled dextran and β-lactamase. Cells that had been successfully permeabilized contained β-lactamase and were red fluorescent when illuminated at the rhodamine excitation wavelength on a fluorescent microscope. The cells were incubated with 5 μM fluorogenic β-lactamase substrate, CCF2/ac$_2$AM$_2$, at room temperature for 30 minutes. Illumination with violet light (405 nm) revealed blue fluorescent and green fluorescent cells. All cells that had taken up the marker rhodamine-dextran appeared fluorescent blue, while cells devoid the enzyme appeared fluorescent green.

Example 3—Use of a α Lactamase substrate

Cells from cell lines of various mammalian origin were transiently transfected with a plasmid containing the RTEM β-lactamase gene under the control of a mammalian promoter. The gene encodes cytosolic β-lactamase lacking any signal sequence and is listed as SEQ. ID. 1. 10 to 48 hours after transfection cells were exposed to 5 micromolar CCF2/ac$_2$AM$_2$ for 1 to 6 hours. In all cases fluorescent blue cells were detected on examination with a fluorescence microscope. Not a single blue fluorescent cell was ever detected in non transfected control cells. To quantitate the fluorescence measurements the cells were first viewed through coumarin (450 DF 65) and then fluorescein (515 EFLP) emission filters and pictures were recorded with a charge couple device camera. The average pixel intensities of CCF2 loaded transfected cells (blue) and controls (green) at coumarin and fluorescein wavelength in COS-7 (Table 2) and CHO (Table 3) cells are summarized; values for 4 representative cells for each population are given. Thus, the substrate CCF2 revealed gene expression in single living mammalian cells. Substrate can be loaded using Pluronic formulations (see Molecular Probes Catalog) using polyethylene glycol.

TABLE 1

COS-7 (origin: SV40 transformed African green monkey kidney cells)

| Table of pixel intensites | | coumarin emission filter | Fluorescein emission filter |
|---|---|---|---|
| Blue cell | #1 | 27 | 20 |
| | #2 | 34 | 23 |
| | #3 | 31 | 31 |
| | #4 | 22 | 33 |
| Green cell | #1 | 4 | 43 |
| | #2 | 4 | 42 |
| | #3 | 5 | 20 |
| | #4 | 3 | 24 |

TABLE 2

CHO (origin: Chinese hamster ovary cells)

| Table of pixel intensites | | coumarin emission filter | Fluorescein emission filter |
|---|---|---|---|
| Blue cell | #1 | 98 | 112 |
| | #2 | 70 | 113 |
| | #3 | 76 | 92 |
| | #4 | 56 | 67 |
| Green cell | #1 | 9 | 180 |
| | #2 | 9 | 102 |
| | #3 | 7 | 101 |
| | #4 | 9 | 83 |

Example 4—Expression of Gα$_{15}$ and Gα$_{16}$ in Cells

This example illustrates that, although constitutive expression of Gα$_{15}$ or Gα$_{16}$ at high levels is toxic to cells, expression of Gα$_{15}$ or Gα$_{16}$ from a gene that is controlled by an inducible promoter, is tolerated by the cells. For constitutive or inducible expression of Gα$_{15}$ or Gα$_{16}$, the genes encoding each of these subunits were placed, separately, under the control of a cytomegalovirus promoter in the plasmids pcDNA3Gα15, pcDNA3Gα16 (Vector pcDNA3 available from Invitrogen, Inc., Del Mar, CA.), pdEF-BOSGα15, and pdE F-BOSGα16 (For pd BOSG, see Gossen and Bujard, 1992, Proc. Natl. Acad. Sci. 89:5547–5551, also available from Clontech). To construct pdEF-BOSG 15 and pdEF-BOSG 16, sequences encoding the G subunit were inserted into pdEFBOS at its EcoRI and NotI sites. The plasmid pdEFBOS was derived from pEF-BOS by removing the HindIII fragment containing the SV40 Ori (see Mizushima and Nagata, 1990, Nucl. Acids. Res. 18). Each of these plasmids was used to transfect COS-7 cells, according to conventional protocols, and each plasmid carried a neo gene, which confers resistance to G418. As is summarized in Table 3, approximately 150 G418-resistant clones were generated, yet none of the clones was able to express a promiscuous G-protein. The ability of a cell to express a promiscuous G-protein was determined by Western blot analysis using an antibody that binds a peptide having the amino acid sequence RPSVLARYLDEINLL (SEQ ID NO: 5) (Amatruda et al., 1991, Proc. Natl. Acad. Sci. 88:5587–5591). These data show that constitutive expression of a promiscuous G-protein under the control of a strong promoter is not tolerated by COS-7 cells. Constitutive expression of promiscuous G proteins at high levels may lead to constant accumulation of inositol phosphates or metabolites, which may be toxic to cells.

TABLE 3

High-Level Constitutive Expression of Promiscuous G-Proteins is not Tolerated

| Construct | Selection | G418-resistant clones picked | Clones expressing $G\alpha_{15/16}$ |
|---|---|---|---|
| PcDNA3Gα15 | G418 | 53 | 0 |
| PcDNA3Gα16 | G418 | 48 | 0 |
| pdEF-BOSGα15 | G418 | 36 | 0 |
| pdEF-BOSGα16 | G418 | 19 | 0 |

The data summarized herein indicate that, although cells may not tolerate constitutive expression of promiscuous Gα proteins at high levels, they can tolerate expression of promiscuous Gα proteins from an inducible promoter. In this case, the genes for $G\alpha_{15}$ and $G\alpha_{16}$ were placed under the control of a cytomegalovirus (CMV) promoter that was operably linked to a heptamerized tet operator (Gossen and Bujard, 1992, Proc. Natl. Acad. Sci. 89:5547–5551). The plasmid encoding Gα and; the plasmid encoding $G\alpha_{16}$ are identical, except sequences encoding $G\alpha_{16}$ in lieu of $G\alpha_{15}$. These plasmids were used to transfect COS-7 cells. These cells were co-transfected with a tetracyclin-dependent transactivator, rtTA, that is operably linked to a CMV promoter of a plasmid that carries a neomycin resistance gene (Gossen et al., 1995, Science 268:1766–1769).

Figure 3:
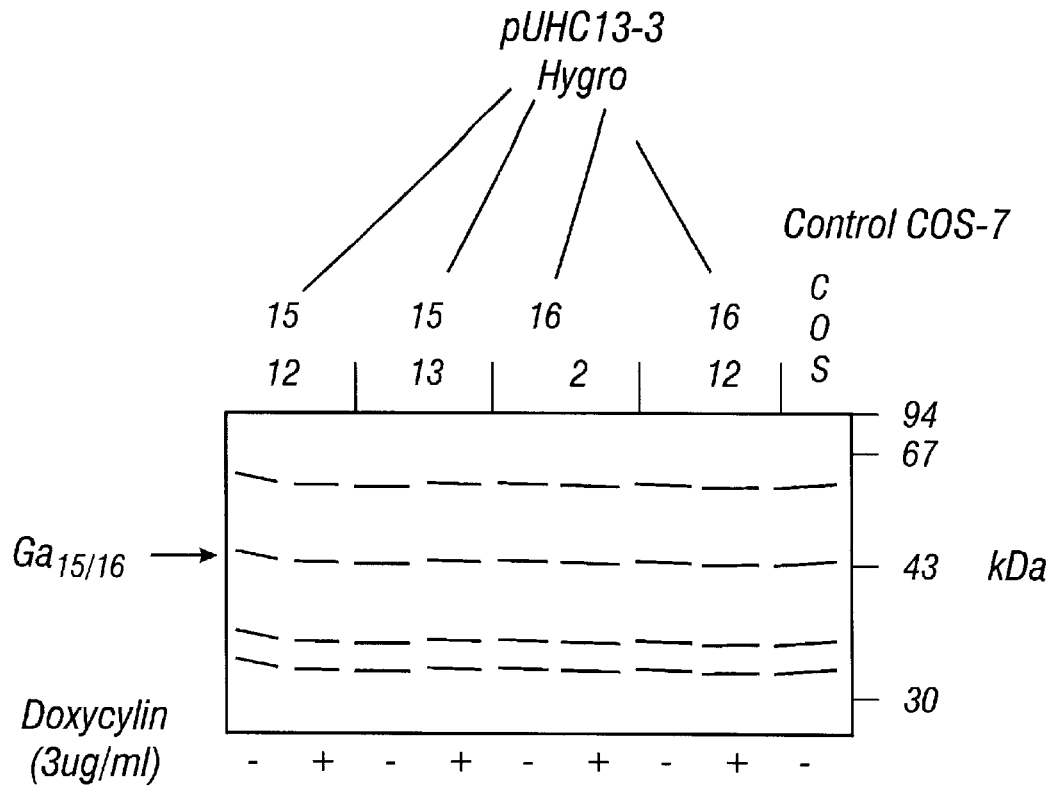
FIG. 3: is a copy of a photograph of a Western blot. Lanes corresponding to samples that lacked or contained doxycyclin are indicated by "−" and "+" respectively. Lanes 1–4 show inducible expression of $G\alpha_{15}$ in two distinct clones of COS-7 cells. Lanes 5–8 show inducible expression of $G\alpha_{16}$ in two distinct clones. $G\alpha_{15}$ and $G\alpha_{16}$ each appear as a species having a molecular weight of approximately 43 kDA in each of the "+" lanes. As a negative control, COS-7 cells were analyzed in lane 9. The predicted molecular weight of Gα subunit is 43–45 kDa.

Expression of the Gα genes was induced by contacting the cells with doxycyclin, a tetracyclin analog. In these experiments, the doxycyclin concentration was 3 g/ml, although doxycyclin concentrations ranging from 0.01 to 10 μml can be used in order to regulate the level of gene expression. Of 17 hygromycin-resistant clones that were analyzed, 2 clones showed doxycyclin-dependent expression of $G\alpha_{15}$ or $G\alpha_{16}$ by Western blot analysis as described above. FIG. 3 illustrates that, in the presence of doxycyclin, expression of $G\alpha_{15}$ or $G\alpha_{16}$ is detectable as a band of approximately 43 kDa. This expression system provides low levels of constitutive expression of $G\alpha_{15}$ or $G\alpha_{16}$ (e.g., less than 100 Gα proteins/cell), yet expression of the Gα protein is highly inducible. Up to 10,000 Gα proteins/cell are produced upon induction of gene expression. As a control, COS-7 cells that lacked the Gα gene were analyzed, and Western blot analysis indicated that the control cells did not express $G\alpha_{15}$ or $G\alpha_{16}$. In sum, these experiments demonstrate that stable cells can be produced by employing an inducible promoter that provides (a) low levels of constitutive expression (i.e., producing less than approximately 100 Gα proteins/cell), and (b) high levels of induced expression (i.e., producing approximately 10,000 Gα proteins/cell).

Example 5—Detection of Gα Protein Activity by Detection of Fluorescence Emission These examples demonstrate that activation of a Gα protein in a cell, and a change in expression of a reporter gene, can be detected by a detecting a change in fluorescence emission of a sample that includes the cell. These examples employ Jurkat T lymphocytes that were transfected with a genetic construct that expresses a reporter gene. The genetic construct includes a NFAT promoter, which is responsive to increased calcium levels and protein kinase C activation that result from activation of Gα protein. The NFAT promoter was operably linked to a β-lactamase reporter gene. To detect expression of the reporter gene, and thereby detect activation of Gα, the cells were contacted with the β-lactamase substrate $CCF2ac_2/AM_2$ (described herein), and fluorescence emission was detected according to previously described methods (Tsien et al., 1993, Trends in Cell Biology 3:242–245).

Two different compounds, ionomycin and phorbol myristate acetate (PMA), were used to optimize detection of expression of the reporter gene in these examples. In the first example, the dose response to ionomycin was measured. In this example, a set of samples of cells were contacted with PMA (at 3 nM) and the calcium ionophore ionomycin (at various concentrations, ranging from 0 to 3.0 μM). Ionomycin increases calcium levels inside of the cells, and thereby increases the probability that activation of a G-protein, and a G-protein-mediated increase in calcium levels, will activate expression of a reporter gene (e.g., a β-lactamase gene) that is operably linked to a calcium-responsive promoter (e.g., a NFAT promoter).

Figure 4A:
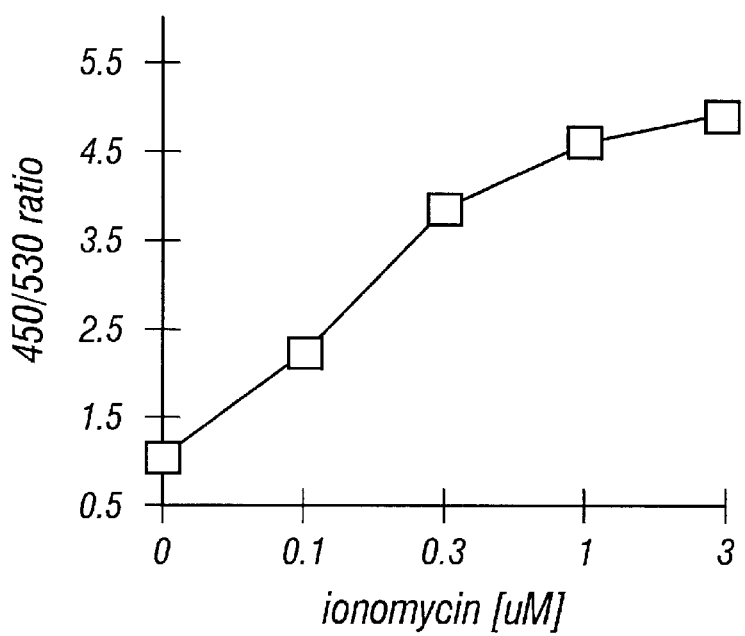
FIGS. 4A–B: is a graph showing the ionomycin dose response, as measured by fluorescence emission of living cells that express β-lactamase reporter gene, and which were contacted with a fluorogenic β-lactamase substrate. Because the NFAT response element usually requires both a calcium increase and protein kinase C activation, these cells were also treated with 10 nm PMA.

In practicing these methods, it is preferable to add the ionophore to a level that is just below the threshold level for activation of the calcium-responsive promoter (e.g., the NFAT promoter). Expression of the reporter gene then is activated by activation of the Gα protein, and the subsequent rise in intracellular calcium levels. As is illustrated in FIG. 4A, fluorescence emission from a sample of the aforementioned cells can be measured by FRET. In this example, fluorescence emission was measured approximately 90 minutes after stimulation. Because the fluorogenic β-lactamase substrate undergoes a shift in fluorescence emission, fluorescence emission is measured as an emission ratio (450/530) when exciting at 400 nm. This figure also illustrates that an ionomycin concentration of approximately 0.3 μM is preferable for increasing the intracellular calcium level to a level that is just below the threshold level for activation of the calcium-responsive promoter.

Figure 4B:
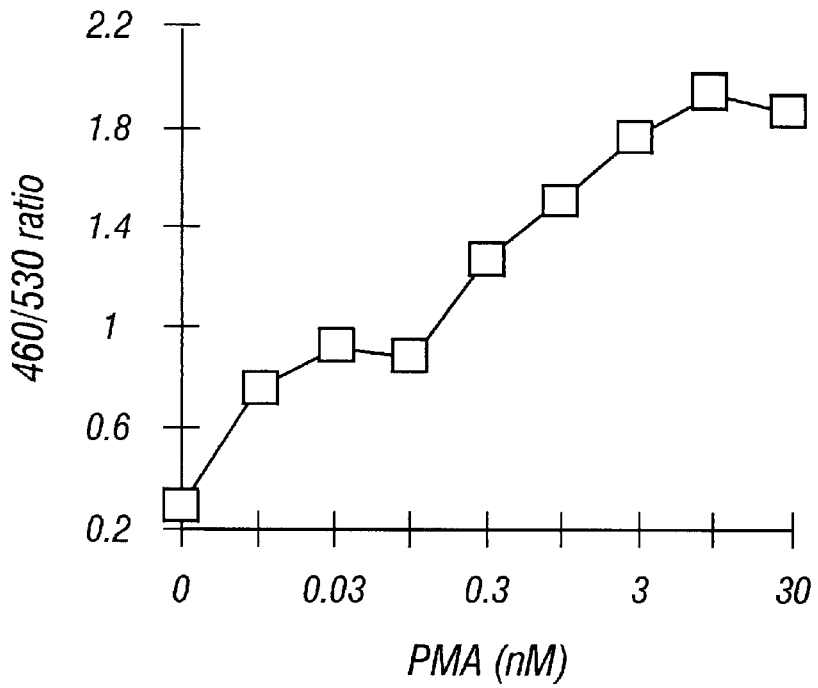
Figure 5:
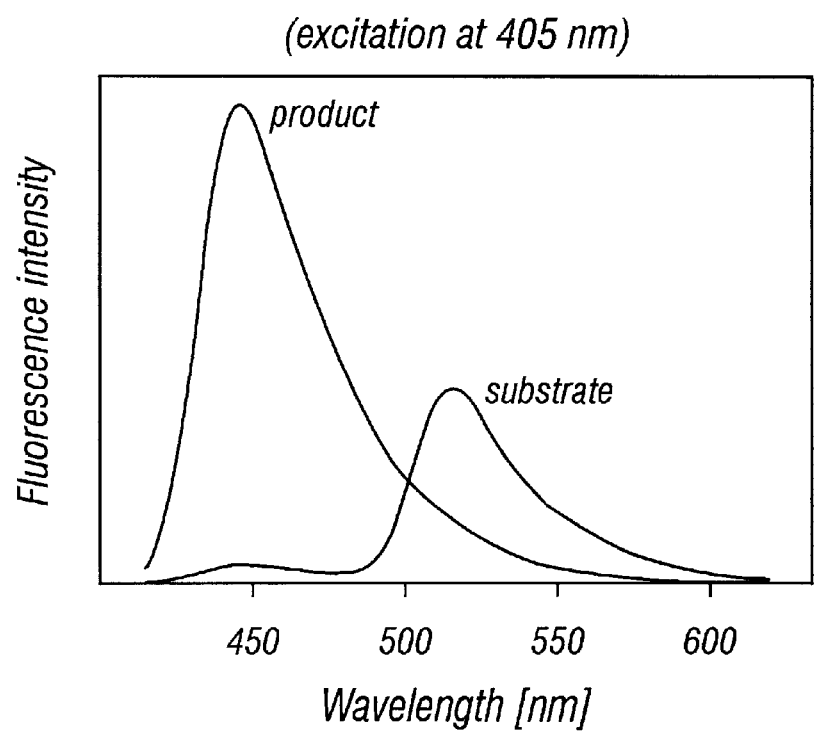
FIG. 5: is a graphic representation of the emission spectrum of the β-lactamase substrate CCF2 before and after it is cleaved by β-lactamase.

In a second example, the dose response of PMA required to stimulate NFAT-driven expression was measured. Although PMA does not, by itself, affect NFAT-regulated gene expression, it potentiates a cell's response to an increase in calcium levels. In this example, a set of cells was treated with ionomycin (at 1 μM ionomycin) and PMA (at various concentrations, ranging from 0 to 30 nM). As above, fluorescence emission was measured 90 minutes after stimulation. As is illustrated in FIG. 4B, increasing concentrations of PMA increased fluorescence emission from the cell sample. Thus, treating the cells with PMA enhances detection of expression of the reporter gene. This example also illustrates that a PMA concentration of approximately 3 nM is preferable for enhancing detection of expression of a reporter gene.

Example 6—Monitoring Activation and Inhibition of GPCR Activity with an NFAT β-Lactamase Assay This example demonstrates that activation of a GPCR (Gq receptor subtype) can be detected with an NFAT β-lactamase assay, which is an example of signal transduction detection system based on a calcium-responsive promoter transcription based assay. Stable cell line (production of described herein) containing Gq-type GPCR receptor expresses β-lactamase in response to the addition of the agonist. The Gαq protein was endogenously expressed. This response is inhibited by an antagonist. Jurkat clones expressing NFAT-β1a were transfected with expression vectors containing the Gq receptor and neomycin resistance gene (double transfection). The transfected population was neo-selected and sorted by FACS for clones responding to the GPCR agonist. For the experiments shown, cells were stimulated for three hours with the indicated ligands. Cells were then loaded with β-lactamase substrate CCF2/ac2AM for 1 hour, washed, dispensed into wells of a microtiter plate (100,000 cells/well) and the blue/green ratio was recorded by a plate reader.

Figure 6:
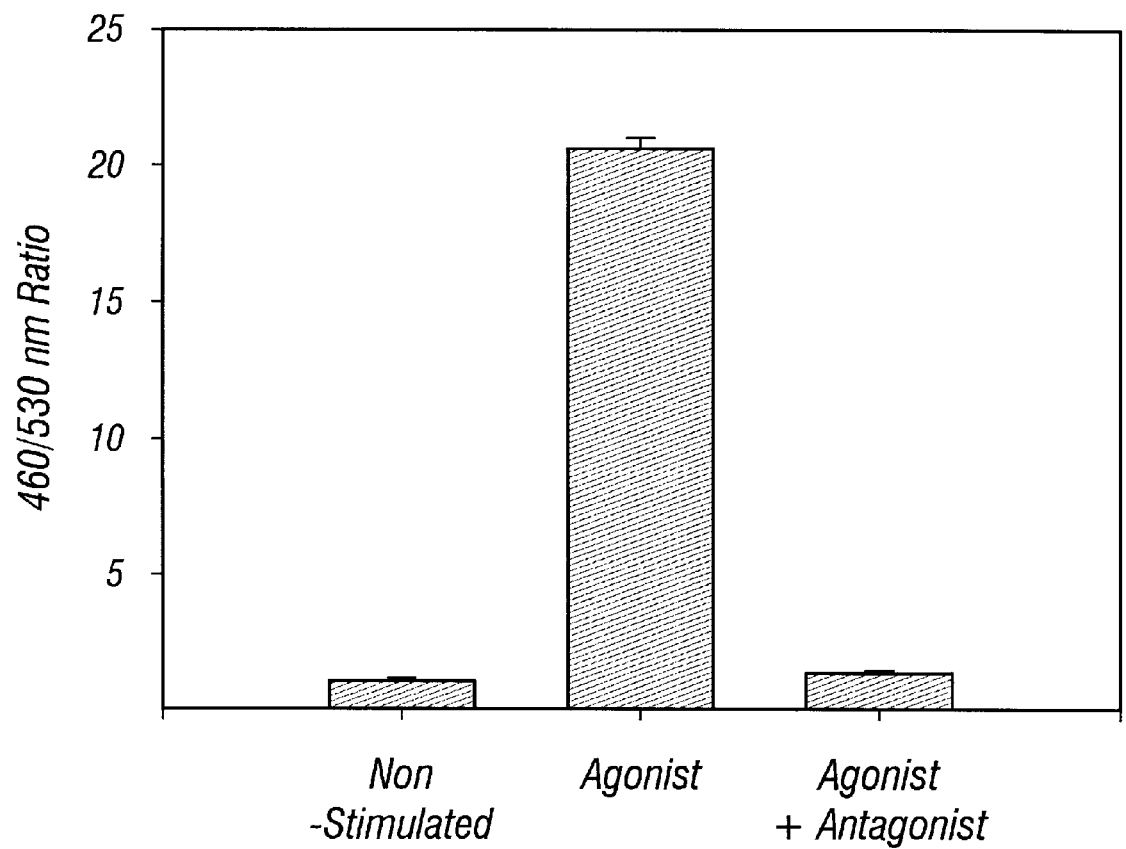
FIG. 6: shows the results of an NFAT β-lactamase transcription based assay using a heterologouly express GPCR (Gq subtype) in the presence of agonist, agonist and antagonist or solvent for agonist ("non-stimulated" control).
Figure 7A:
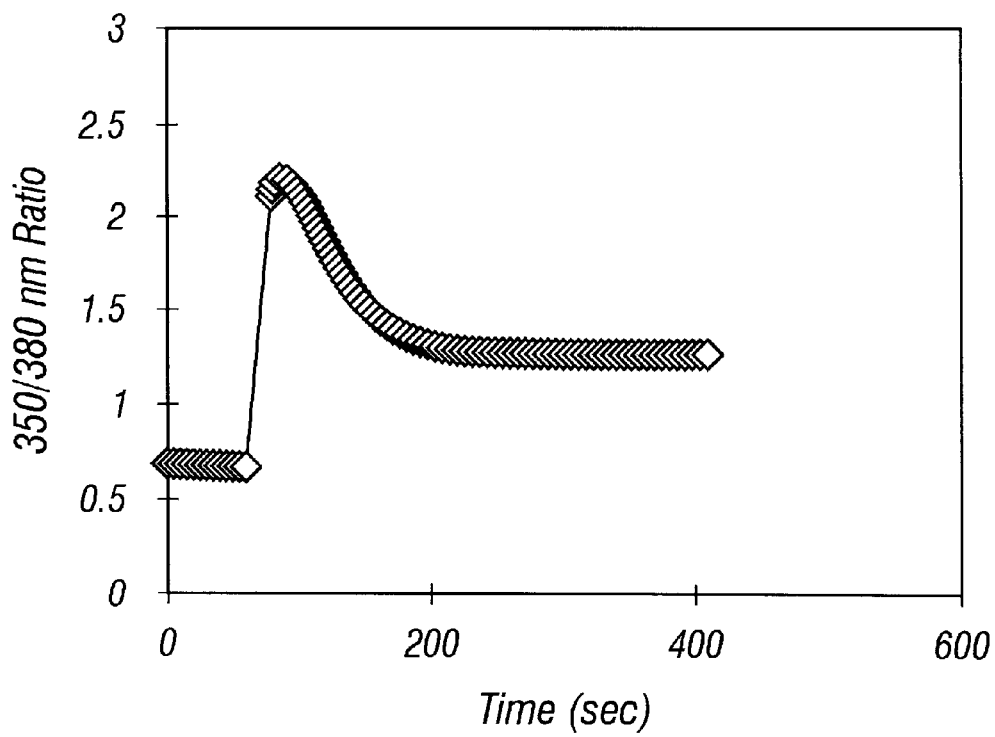
FIGS. 7A–F: shows activation of a Gαs subtype GPCR (panels A–C) and a Gαi subtype GPCR (panels D–F) using promiscuous Gα protein in a cell-based (transient transfection of all constructs) calcium indicator assay (FURA-PE3).
Figure 7B:
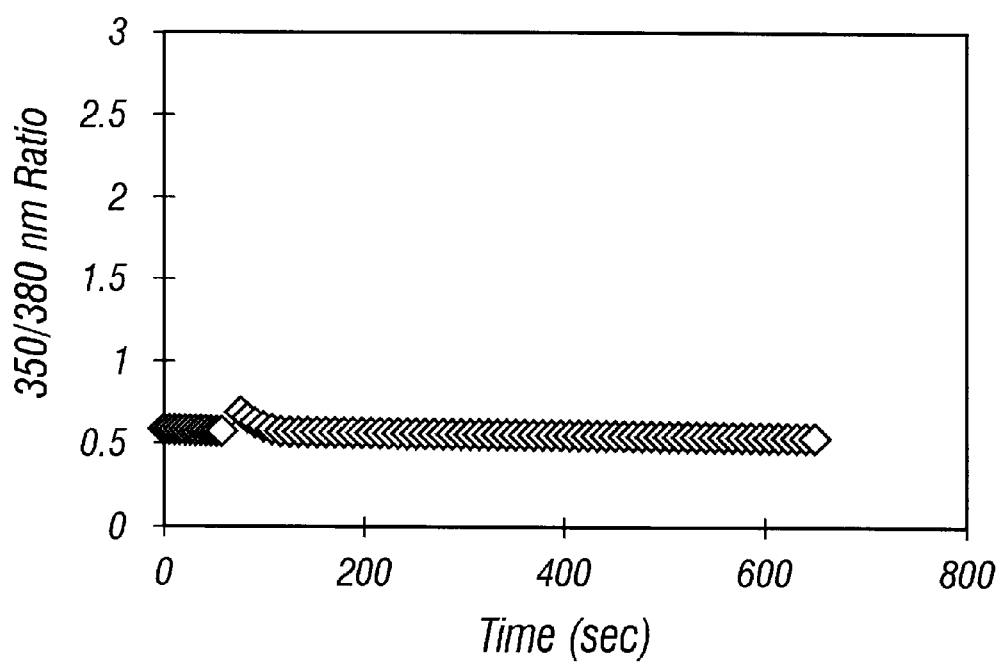
Figure 7C:
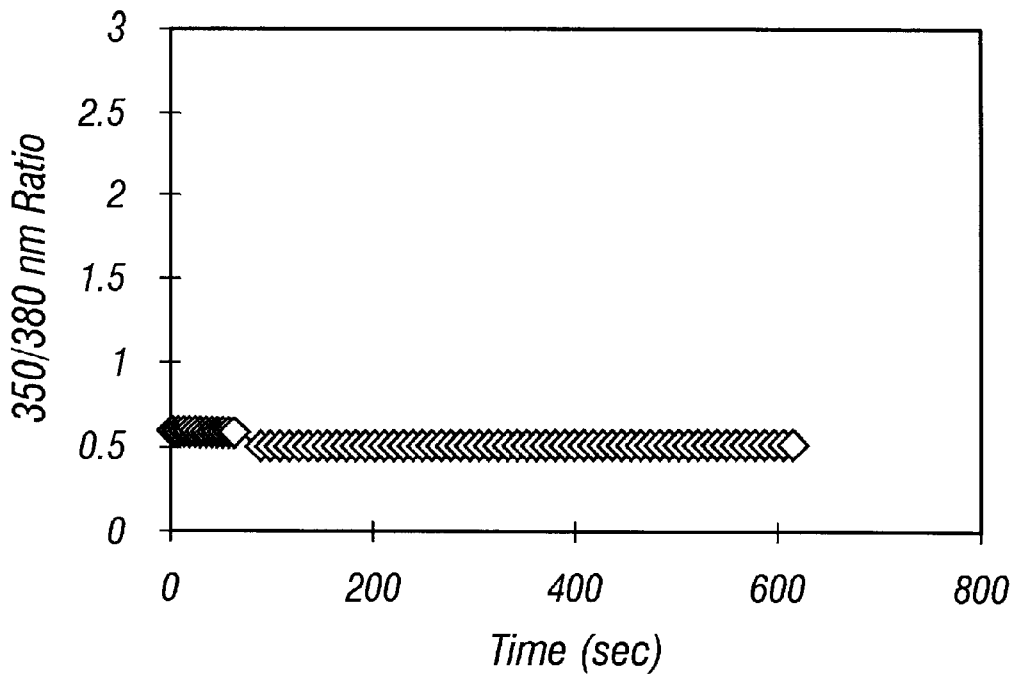
Figure 7D:
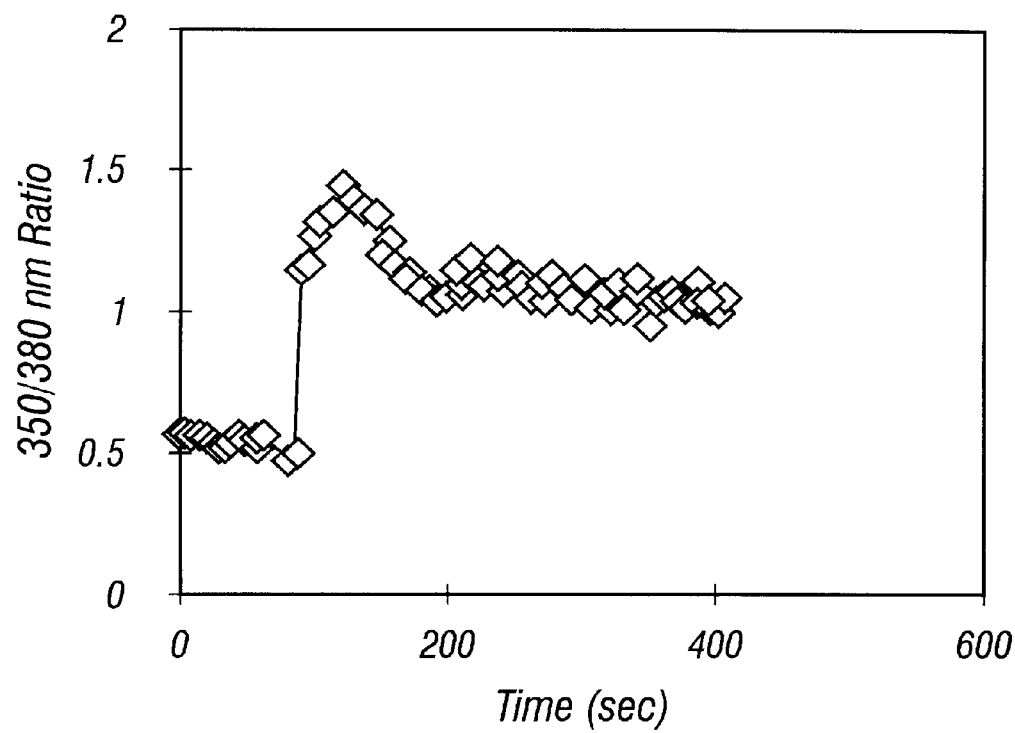
Figure 7E:
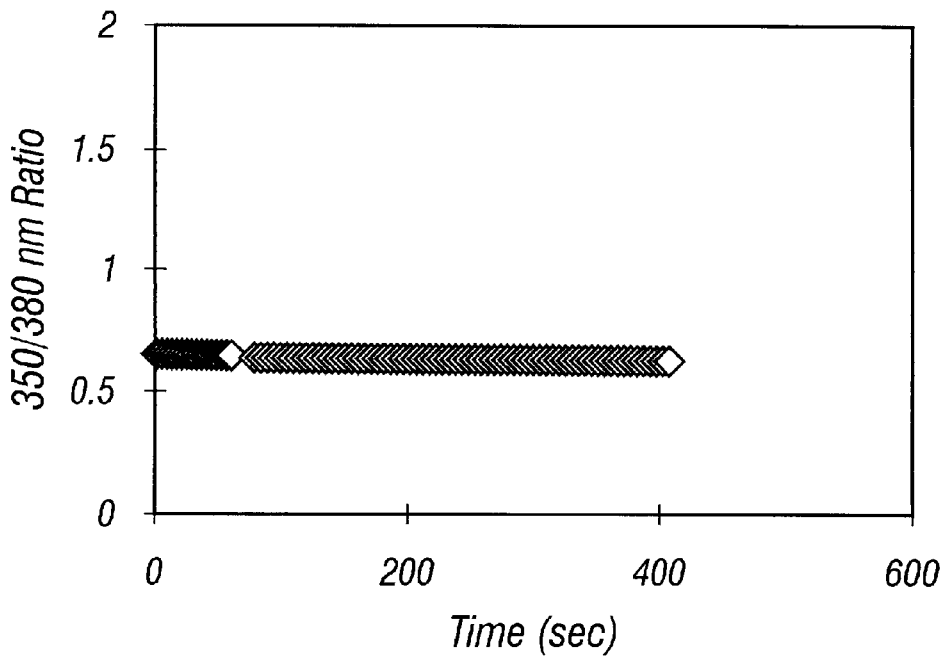
Figure 7F:
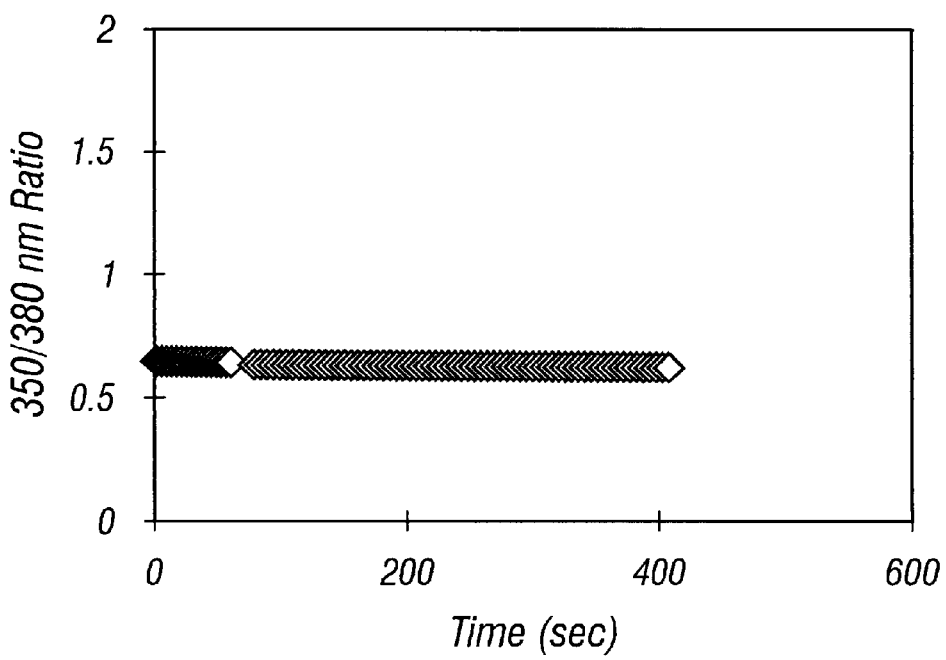

FIG. 6 demonstrates a twenty-fold change in signal upon receptor activation with an agonist (saturating dose 100 $\mu$M). A receptor antagonist (10 $\mu$M) completely inhibited the agonist activation of the receptor.

Example 7—Monitoring Activation of GPCRs with a Calcium Dye (transiently transfected cells)

This example demonstrates that activation of GPCRs (Gs and Gi receptor subtypes) can be detected with an intracellular calcium indicator transiently transfected cells, which is an example of a signal transduction detection system based on changes in intracellular ions. The cells used were transiently transfected with two constructs. $4 \times 10^5$ CHO-K1 cells were seeded on 35 mm petri dishes one day before transfection. 5 $\mu$g plasmid DNA and 12 $\mu$l lipofectamine were added for each dish using the stand method. In some cases, pBluescripts (−) or KS⁻ plasmid was used to keep the amount of DNA consistent between each transfection. 20 h later, the cells were stained with 10 mM Fura-PE3 (Molecular Probe) for 3 h. Imaging analysis of calcium was performed to measure the $[Ca^{2+}]$ signal mediated by the agonists addition.

Following imaging data show that the promiscuous Gα16 couples a Gs-receptor and a Gi-receptor in CHO-K1 cells following transient transfections. The data also show that promiscuous Gα protein can change the effector downstream of the GPCR. Panel A: 60 seconds after starting of the experiment, 10 $\mu$M agonist solution was added to the cells transfected by pCIS/Gα16 (CMV promoter) and Gs-receptor (CMV promoter) expression plasmids. Panel B: 60 seconds after starting of the experiment, 10 $\mu$M agonist solution was added to the cells transfected by pCIS/Gα16 alone. Panel C: 60 seconds after starting of the experiment, 10 $\mu$M agonist solution was added to the cells transfected by Gs receptor expression plasmid alone. Panel D: 60 seconds after starting of the experiment, 10 $\mu$M agonist solution was added to the cells transfected by pCIS/Gα16 and Gi-receptor expression plasmids. Panel E: 60 seconds after starting of the experiment, 10 $\mu$M agonist solution was added to the cells transfected by pCIS/Gα16 alone. Panel F: 60 seconds after starting of the experiment, 10 $\mu$M agonist solution was added to the cells transfected by Gi-receptor expression plasmid alone.

Example 8—Monitoring Activation of a GPCR with a Calcium Dye (stably transfected cells)

This example demonstrates that activation of a GPCR (Gs receptor subtype) can be detected with an intracellular calcium indicator in stably transfected cells, which is an example of a signal transduction detection system based on changes in intracellular ions. The cells used were transiently stably with two constructs. Although many cells do not tolerate stable expression of promiscuous Gα protein, such as described herein, surprisingly even cells thought not to tolerate stable expression of promiscuous Gα protein can be sorted using a signal transduction detection system. Such sorting can be performed with a high throughput sorting system, such as a FACS or 96 well imaging system. Typically, the frequency of usable stable cells is about 1 to 2 percent of those cells screened. Functional assay selection of promiscuous Gα protein/GPCR double transfected cells is a preferred method of identifying cells that either tolerate, or express the proper amounts, of promiscuous Gα protein and a GPCR.

Stable CHO-K1 cell lines expressing Gα15-Hyg alone, the Gs-receptor-Neo alone and both the Gα 15 (CMV promoter) and the Gs receptor (CMV promoter) (double transfection), were generated. 48 h after transfection (described herein for the method of lipofectamine-mediated transfection), media containing Hygromycin (0.5 mg/ml), Neomycin (1 mg/ml) or both were added on to the cells to select the stable transformants. 12–15 days after selection, the stable clones were examined using the calcium imaging assays.

The following imaging data show that the promiscuous Gα15 couples a Gs-receptor in CHO-K1 cells following stable cell line generation. The data also show that promiscuous Gα protein can change the effector downstream of the GPCR. Panel A: Calcium imaging of the Gα15/Gs-receptor dual stable clone-2. 10 $\mu$M agonist was added 40 seconds after the starting of the experiment. Panel B: Calcium imaging of the Gs-receptor stable clone -2. 10 $\mu$M agonist was added 40 seconds after the starting of the experiment. Panel C: Calcium imaging of the Gα15 stable clone-H. 10 $\mu$M agonist was added 40 seconds after the starting of the experiment.

Although the invention has been described with reference to the presently preferred embodiments, it should be understood that various modifications can be made without departing from the spirit of the invention. Accordingly, the invention is limited only by the following claims.

REFERENCES

Bram, R. J. and G. R. Crabtree. (1994) Nature 371:355–358.
Offermanns, S. and M. I. Simon. (1995) J. Biol. Chem. 270(25): 15175–15180.
Fiering, S., Northrop, J. P., Nolan, G. P., Mattila, P. S., Crabtree, G. R., and Herzenberg, L. A. (1990) Genes Dev. 4, 1823–1834.
Flanagan, W. F., Corthesy, B., Bram, R. J. and Crabtree, G. R. (1991) Nature 352:803–807.
Gossen, M., Freundlieb, S., Bender, G., Muller, G., Hillen, W., and H. Bujard (1995) Science 268: 1766–1769.
Grinkiewicz, G., Poenie, M., and Tsien, R. Y. (1985) J. Biol. Chem. 260:3440–3450.
Neer, E. J. (1995). Cell, 80:249–257.
Negulescu, P. A., Shastri, N., Cahalan, Michael D. (1994). Proc. Nat. Acad Sci. 91:2873–2877.
Sternweis, P. C. and A. V. Smrcka (1992) Trends Biochem. Sci. 17:502–506.
Thastrup, O., Cullen, P. J., Drobak, B. K., Hanley, M. R., and Dawson, A. P. (1990) Proc. Natl. Acad. Sci. 87:2466–2470.
Tsien, R. Y., Backsai, B. J., and Adams, S. R. (1993) Trends Cell Biol. 3:242–245.

All publications, including patent documents and scientific articles, referred to in this application are incorporated by reference in their entirety for all purposes to the same extent as if each individual publication were individually incorporated by reference.

What is claimed is:

1. A stable isolated mammalian cell, comprising;
    a) a first heterologous promoter operably linked to a first polynucleotide encoding a Gα15 protein,
    b) a second heterologous promoter operably linked to a second polynucleotide encoding a GPCR not naturally expressed in said cell, and
    c) a third heterologous promoter operably linked to a third polynucleotide encoding a reporter gene,
    wherein said isolated mammalian cell stably expresses said Gα15 protein at sufficient levels to permit promiscuous coupling to said GPCR, and
    wherein said third heterologous promoter is directly or indirectly modulated by the activity of said Gα15 protein.

2. The cell of claim 1, wherein said cell is selected from the group consisting of BHK cells, mouse L cells, Jurkat cells, 153DG44 cells, HEK cells, CHO cells, PC12 cells, human T-lymphocyte cells and Cos-7 cells.

3. The cell of claim 1, wherein said first heterologous promoter comprises an inducible promoter.

4. The cell of claim 3, wherein said inducible promoter comprises a tet operator.

5. The cell of claim 1, wherein said third heterologous promoter comprises a protein kinase C- responsive promoter.

6. The cell of claim 1, wherein said third heterologous promoter is indirectly modulated by the activity of said promiscuous Gα15 protein.

7. The cell of claim 1, wherein said third heterologous promoter comprises a calcium-responsive promoter.

8. The cell of claim 7, wherein said calcium-responsive promoter comprises a nuclear factor of activated T cell promoter.

9. The cell of claim 1, wherein said first polynucleotide comprises the nucleotide sequence of SEQ ID NO.2.

10. The cell of claim 1, wherein the reporter gene encodes a reporter selected from the group consisting of luciferase, green fluorescent protein, chloramphenicol acetyl transferase, β-galactosidase, alkaline phosphatase, β-lactamase, and human growth hormone.

11. The cell of claim 1, wherein said GPCR is from a cDNA.

12. The cell of claim 1, wherein said cell is selected from a cell line subjected to functional cell analysis with a signal transduction detection system.

13. The cell of claim 1, wherein said GPCR is substantially coupled to either $G\alpha_i$, $G\alpha_s$ or $G\alpha_{12}$ in the absence of said Gα15 protein.

14. A kit comprising assay reagents and a container containing a cell of claim 13.

15. A stable isolated mammalian cell, comprising:
   a) a first heterologous promoter operably linked to a first polynucleotide encoding a Gα15 protein,
   b) a second heterologous promoter operably linked to a second polynucleotide encoding a reporter gene, and
   c) a GPCR wherein said GPCR is not coupled to said reporter gene in the absence of said Gα15 protein,
      wherein said isolated mammalian cell stably expresses said Gα15 protein at sufficient levels to permit promiscuous coupling to said GPCR, and
      wherein said second heterolgous promoter is directly or indirectly modulated by the activity of said Gα15 protein.

16. The cell of claim 15, wherein said cell is selected from the group consisting of BHK cells, mouse L cells, Jurkat cells, 153DG44 cells, HEK cells, CHO cells, PC12 cells, human T-lymphocyte cells and Cos-7 cells.

17. The cell of claim 15, wherein said first heterolosous promoter comprises an inducible promoter.

18. The cell of claim 17, further comprising a GPCR modulator and a test chemical.

19. The cell of claim 15, wherein said second heterologous promoter is indirectly modulated by the activity of said promiscuous Gα15 protein.

20. The cell of claim 15, wherein said second heterologous promoter is directly modulated by the activity of said promiscuous Gα15 protein.

21. The cell of claim 15, wherein said second heterologous promoter comprises a calcium-responsive promoter.

22. The cell of claim 21, wherein said calcium-responsive promoter comprises a nuclear factor of activated T cell promoter.

23. The cell of claim 15, wherein said first polynucleotide has the nucleotide sequence of SEQ ID NO: 2, and wherein said cell further comprises a test compound.

24. The cell of claim 15, wherein said first polynucleoride comprises SEQ ID NO: 2.

25. The cell of claim 24, wherein said reporter gene encodes β-lactamase or β-galactosidase.

26. An isolated mammalian cell comprising:
   a) a first heterologous promoter operably linked to a first polynucleotide encoding a Gα15 protein,
   b) a second heterologous promoter operably linked to a second polynucleotide encoding a GPCR not naturally expressed in said cell,
   c) a signal transduction detection system that comprises a dye,
   wherein said GPCR is substantially coupled to either $G\alpha_i$, $G\alpha$ or $G\alpha_{12}$ in the absence of said Gα15 protein, and
   wherein said isolated mammalian cell stably expresses said Gα15 protein at sufficient levels to permit promiscuous coupling to said GPCR.

27. The cell of claim 26, further comprising an intracellular calcium indicator.

* * * * *

UNITED STATES PATENT AND TRADEMARK OFFICE
CERTIFICATE OF CORRECTION

PATENT NO. : 6,004,808
APPLICATION NO. : 08/878801
DATED : December 21, 1999
INVENTOR(S) : Paul Negulescu et al.

It is certified that error appears in the above-identified patent and that said Letters Patent is hereby corrected as shown below:

Claim 17, column 41, line 33, cancel "heterolosous" and insert --heterologous--

Claim 24, column 42, line 15, cancel "polynucleoride" and insert --polynucleotide--

Claim 26, column 42, line 29, cancel "Gα" and insert --$G\alpha_S$--

Signed and Sealed this
Third Day of April, 2012

David J. Kappos
*Director of the United States Patent and Trademark Office*

SEQUENCE LISTING

<160> NUMBER OF SEQ ID NOS: 4

<210> SEQ ID NO 1
<211> LENGTH: 1125
<212> TYPE: DNA
<213> ORGANISM: Mus musculus
<220> FEATURE:
<221> NAME/KEY: CDS
<222> LOCATION: (1)...(1122)

<400> SEQUENCE: 1

```
atg gcc cgc tcg ctg acc tgg cgc tgc tgc ccc tgg tgc ctg acg gag        48
Met Ala Arg Ser Leu Thr Trp Arg Cys Cys Pro Trp Cys Leu Thr Glu
 1               5                  10                  15 gat gag aag gcc gcc gcc cgg gtg gac cag gag atc aac agg atc ctc        96
Asp Glu Lys Ala Ala Ala Arg Val Asp Gln Glu Ile Asn Arg Ile Leu
                20                  25                  30 ttg gag cag aag aag cag gac cgc ggg gag ctg aag ctg ctg ctt ttg       144
Leu Glu Gln Lys Lys Gln Asp Arg Gly Glu Leu Lys Leu Leu Leu Leu
            35                  40                  45 ggc cca ggc gag agc ggg aag agc acc ttc atc aag cag atg cgg atc       192
Gly Pro Gly Glu Ser Gly Lys Ser Thr Phe Ile Lys Gln Met Arg Ile
        50                  55                  60 atc cac ggc gcc ggc tac tcg gag gag gag cgc aag ggc ttc cgg ccc       240
Ile His Gly Ala Gly Tyr Ser Glu Glu Glu Arg Lys Gly Phe Arg Pro
 65                  70                  75                  80 ctg gtc tac cag aac atc ttc gtg tcc atg cgg gcc atg atc gag gcc       288
Leu Val Tyr Gln Asn Ile Phe Val Ser Met Arg Ala Met Ile Glu Ala
                85                  90                  95 atg gag cgg ctg cag att cca ttc agc agg ccc gag agc aag cac cac       336
Met Glu Arg Leu Gln Ile Pro Phe Ser Arg Pro Glu Ser Lys His His
               100                 105                 110 gct agc ctg gtc atg agc cag gac ccc tat aaa gtg acc acg ttt gag       384
Ala Ser Leu Val Met Ser Gln Asp Pro Tyr Lys Val Thr Thr Phe Glu
            115                 120                 125 aag cgc tac gct gcg gcc atg cag tgg ctg tgg agg gat gcc ggc atc       432
Lys Arg Tyr Ala Ala Ala Met Gln Trp Leu Trp Arg Asp Ala Gly Ile
        130                 135                 140 cgg gcc tgc tat gag cgt cgg cgg gaa ttc cac ctg ctc gat tca gcc       480
Arg Ala Cys Tyr Glu Arg Arg Arg Glu Phe His Leu Leu Asp Ser Ala
145                 150                 155                 160 gtg tac tac ctg tcc cac ctg gag cgc atc acc gag gag ggc tac gtc       528
Val Tyr Tyr Leu Ser His Leu Glu Arg Ile Thr Glu Glu Gly Tyr Val
                165                 170                 175 ccc aca gct cag gac gtg ctc cgc agc cgc atg ccc acc act ggc atc       576
Pro Thr Ala Gln Asp Val Leu Arg Ser Arg Met Pro Thr Thr Gly Ile
            180                 185                 190 aac gag tac tgc ttc tcc gtg cag aaa acc aac ctg cgg atc gtg gac       624
Asn Glu Tyr Cys Phe Ser Val Gln Lys Thr Asn Leu Arg Ile Val Asp
        195                 200                 205 gtc ggg ggc cag aag tca gag cgt aag aaa tgg atc cat tgt ttc gag       672
Val Gly Gly Gln Lys Ser Glu Arg Lys Lys Trp Ile His Cys Phe Glu
    210                 215                 220 aac gtg atc gcc ctc atc tac ctg gcc tca ctg agt gaa tac gac cag       720
Asn Val Ile Ala Leu Ile Tyr Leu Ala Ser Leu Ser Glu Tyr Asp Gln
225                 230                 235                 240 tgc ctg gag gag aac aac cag gag aac cgc atg aag gag agc ctc gca       768
Cys Leu Glu Glu Asn Asn Gln Glu Asn Arg Met Lys Glu Ser Leu Ala
                245                 250                 255 ttg ttt ggg act atc ctg gaa cta ccc tgg ttc aaa agc aca tcc gtc       816
```

```
Leu Phe Gly Thr Ile Leu Glu Leu Pro Trp Phe Lys Ser Thr Ser Val
                260                 265                 270 atc ctc ttt ctc aac aaa acc gac atc ctg gag gag aaa atc ccc acc      864
Ile Leu Phe Leu Asn Lys Thr Asp Ile Leu Glu Glu Lys Ile Pro Thr
                275                 280                 285 tcc cac ctg gct acc tat ttc ccc agt ttc cag ggc cct aag cag gat      912
Ser His Leu Ala Thr Tyr Phe Pro Ser Phe Gln Gly Pro Lys Gln Asp
            290                 295                 300 gct gag gca gcc aag agg ttc atc ctg gac atg tac acg agg atg tac      960
Ala Glu Ala Ala Lys Arg Phe Ile Leu Asp Met Tyr Thr Arg Met Tyr
305                 310                 315                 320 acc ggg tgc gtg gac ggc ccc gag ggc agc aag aag ggc gca cga tcc     1008
Thr Gly Cys Val Asp Gly Pro Glu Gly Ser Lys Lys Gly Ala Arg Ser
                325                 330                 335 cga cgc ctt ttc agc cac tac aca tgt gcc aca gac aca cag aac atc     1056
Arg Arg Leu Phe Ser His Tyr Thr Cys Ala Thr Asp Thr Gln Asn Ile
                340                 345                 350 cgc aag gtc ttc aag gac gtg cgg gac tcg gtg ctc gcc cgc tac ctg     1104
Arg Lys Val Phe Lys Asp Val Arg Asp Ser Val Leu Ala Arg Tyr Leu
                355                 360                 365 gac gag atc aac ctg ctg tga                                         1125
Asp Glu Ile Asn Leu Leu
            370

<210> SEQ ID NO 2
<211> LENGTH: 374
<212> TYPE: PRT
<213> ORGANISM: Mus musculus

<400> SEQUENCE: 2

Met Ala Arg Ser Leu Thr Trp Arg Cys Cys Pro Trp Cys Leu Thr Glu
 1               5                  10                  15

Asp Glu Lys Ala Ala Ala Arg Val Asp Gln Glu Ile Asn Arg Ile Leu
                20                  25                  30

Leu Glu Gln Lys Lys Gln Asp Arg Gly Glu Leu Lys Leu Leu Leu Leu
            35                  40                  45

Gly Pro Gly Glu Ser Gly Lys Ser Thr Phe Ile Lys Gln Met Arg Ile
        50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
                100                 105                 110

Ala Ser Leu Val Met Ser Gln Asp Pro Tyr Lys Val Thr Thr Phe Glu
            115                 120                 125

Lys Arg Tyr Ala Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220
```

```
Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
            245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
        290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
            325                 330                 335

Arg Arg Leu Phe Ser His Tyr Thr Cys Ala Thr Asp Thr Gln Asn Ile
            340                 345                 350

Arg Lys Val Phe Lys Asp Val Arg Asp Ser Val Leu Ala Arg Tyr Leu
            355                 360                 365

Asp Glu Ile Asn Leu Leu
        370
```

<210> SEQ ID NO 3
<211> LENGTH: 1125
<212> TYPE: DNA
<213> ORGANISM: Homo sapiens
<220> FEATURE:
<221> NAME/KEY: CDS
<222> LOCATION: (1)...(1122)

<400> SEQUENCE: 3

```
atg gcc cgg tcc ctg act tgg ggc tgc tgt ccc tgg tgc ctg aca gag      48
Met Ala Arg Ser Leu Thr Trp Gly Cys Cys Pro Trp Cys Leu Thr Glu
 1               5                  10                  15 gag gag aag act gcc gcc aga atc gac cag gag atc aac agg att ttg      96
Glu Glu Lys Thr Ala Ala Arg Ile Asp Gln Glu Ile Asn Arg Ile Leu
             20                  25                  30 ttg gaa cag aaa aaa caa gag cgc gag gaa ttg aaa ctc ctg ctg ttg     144
Leu Glu Gln Lys Lys Gln Glu Arg Glu Glu Leu Lys Leu Leu Leu Leu
         35                  40                  45 ggg cct ggt gag agc ggg aag agt acg ttc atc aag cag atg cgc atc     192
Gly Pro Gly Glu Ser Gly Lys Ser Thr Phe Ile Lys Gln Met Arg Ile
 50                  55                  60 att cac ggt gtg ggc tac tcg gag gag gac cgc aga gcc ttc cgg ctg     240
Ile His Gly Val Gly Tyr Ser Glu Glu Asp Arg Arg Ala Phe Arg Leu
 65                  70                  75                  80 ctc atc tac cag aac atc ttc gtc tcc atg cag gcc atg ata gat gcg     288
Leu Ile Tyr Gln Asn Ile Phe Val Ser Met Gln Ala Met Ile Asp Ala
                 85                  90                  95 atg gac cgg ctg cag atc ccc ttc agc agg cct gac agc aag cag cac     336
Met Asp Arg Leu Gln Ile Pro Phe Ser Arg Pro Asp Ser Lys Gln His
            100                 105                 110 gcc agc cta gtg atg acc cag gac ccc tat aaa gtg agc aca ttc gag     384
Ala Ser Leu Val Met Thr Gln Asp Pro Tyr Lys Val Ser Thr Phe Glu
        115                 120                 125 aag cca tat gca gtg gcc atg cag tac ctg tgg cgg gac gcg ggc atc     432
Lys Pro Tyr Ala Val Ala Met Gln Tyr Leu Trp Arg Asp Ala Gly Ile
    130                 135                 140 cgt gca tgc tac gag cga agg cgt gaa ttc cac ctt ctg gac tcc gcg     480
Arg Ala Cys Tyr Glu Arg Arg Arg Glu Phe His Leu Leu Asp Ser Ala
```

| | | | | | | | | | | | | | | | | |
|---|---|---|---|---|---|---|---|---|---|---|---|---|---|---|---|---|
| | 145 | | | | 150 | | | | | 155 | | | | 160 | | |
| gtg | tat | tac | ctg | tca | cac | ctg | gag | cgc | ata | tca | gag | gac | agc | tac | atc | 528 |
| Val | Tyr | Tyr | Leu | Ser | His | Leu | Glu | Arg | Ile | Ser | Glu | Asp | Ser | Tyr | Ile | |
| | | | | 165 | | | | | 170 | | | | | 175 | | |
| ccc | act | gcg | caa | gac | gtg | ctg | cgc | agt | cgc | atg | ccc | acc | aca | ggc | atc | 576 |
| Pro | Thr | Ala | Gln | Asp | Val | Leu | Arg | Ser | Arg | Met | Pro | Thr | Thr | Gly | Ile | |
| | | | 180 | | | | | 185 | | | | | 190 | | | |
| aat | gag | tac | tgc | ttc | tcc | gtg | aag | aaa | acc | aaa | ctg | cgc | atc | gtg | gat | 624 |
| Asn | Glu | Tyr | Cys | Phe | Ser | Val | Lys | Lys | Thr | Lys | Leu | Arg | Ile | Val | Asp | |
| | | 195 | | | | | 200 | | | | | 205 | | | | |
| gtt | ggt | ggc | cag | agg | tca | gag | cgt | agg | aaa | tgg | att | cac | tgt | ttc | gag | 672 |
| Val | Gly | Gly | Gln | Arg | Ser | Glu | Arg | Arg | Lys | Trp | Ile | His | Cys | Phe | Glu | |
| | 210 | | | | | 215 | | | | | 220 | | | | | |
| aac | gtg | att | gcc | ctc | atc | tac | ctg | gcc | tcc | ctg | agc | gag | tat | gac | cag | 720 |
| Asn | Val | Ile | Ala | Leu | Ile | Tyr | Leu | Ala | Ser | Leu | Ser | Glu | Tyr | Asp | Gln | |
| 225 | | | | | 230 | | | | | 235 | | | | | 240 | |
| tgc | cta | gag | gag | aac | gat | cag | gag | aac | cgc | atg | gag | gag | agt | ctc | gct | 768 |
| Cys | Leu | Glu | Glu | Asn | Asp | Gln | Glu | Asn | Arg | Met | Glu | Glu | Ser | Leu | Ala | |
| | | | | 245 | | | | | 250 | | | | | 255 | | |
| ctg | ttc | agc | acg | atc | cta | gag | ctg | ccc | tgg | ttc | aag | agc | acc | tcg | gtc | 816 |
| Leu | Phe | Ser | Thr | Ile | Leu | Glu | Leu | Pro | Trp | Phe | Lys | Ser | Thr | Ser | Val | |
| | | | 260 | | | | | 265 | | | | | 270 | | | |
| atc | ctc | ttc | ctc | aac | aag | acg | gac | atc | ctg | gaa | gat | aag | att | cac | acc | 864 |
| Ile | Leu | Phe | Leu | Asn | Lys | Thr | Asp | Ile | Leu | Glu | Asp | Lys | Ile | His | Thr | |
| | | 275 | | | | | 280 | | | | | 285 | | | | |
| tcc | cac | ctg | gcc | aca | tac | ttc | ccc | agc | ttc | cag | gga | ccc | cgg | cga | gac | 912 |
| Ser | His | Leu | Ala | Thr | Tyr | Phe | Pro | Ser | Phe | Gln | Gly | Pro | Arg | Arg | Asp | |
| | 290 | | | | | 295 | | | | | 300 | | | | | |
| gca | gag | gcc | gcc | aag | agc | ttc | atc | ttg | gac | atg | tat | gcg | cgc | gtg | tac | 960 |
| Ala | Glu | Ala | Ala | Lys | Ser | Phe | Ile | Leu | Asp | Met | Tyr | Ala | Arg | Val | Tyr | |
| 305 | | | | | 310 | | | | | 315 | | | | | 320 | |
| gcg | agc | tgc | gca | gag | ccc | cag | gac | ggt | ggc | agg | aaa | ggc | tcc | cgc | gcg | 1008 |
| Ala | Ser | Cys | Ala | Glu | Pro | Gln | Asp | Gly | Gly | Arg | Lys | Gly | Ser | Arg | Ala | |
| | | | | 325 | | | | | 330 | | | | | 335 | | |
| cgc | cgc | ttc | ttc | gca | cac | ttc | acc | tgt | gcc | acg | gac | acg | caa | agc | gtc | 1056 |
| Arg | Arg | Phe | Phe | Ala | His | Phe | Thr | Cys | Ala | Thr | Asp | Thr | Gln | Ser | Val | |
| | | | 340 | | | | | 345 | | | | | 350 | | | |
| cgc | agc | gtg | ttc | aag | gac | gtg | cgg | gac | tcg | gtg | ctg | gcc | cgg | tac | ctg | 1104 |
| Arg | Ser | Val | Phe | Lys | Asp | Val | Arg | Asp | Ser | Val | Leu | Ala | Arg | Tyr | Leu | |
| | | 355 | | | | | 360 | | | | | 365 | | | | |
| gac | gag | atc | aac | ctg | ctg | tga | | | | | | | | | | 1125 |
| Asp | Glu | Ile | Asn | Leu | Leu | | | | | | | | | | | |
| | 370 | | | | | | | | | | | | | | | |

<210> SEQ ID NO 4
<211> LENGTH: 374
<212> TYPE: PRT
<213> ORGANISM: Homo sapiens

<400> SEQUENCE: 4

| | | | | | | | | | | | | | | |
|---|---|---|---|---|---|---|---|---|---|---|---|---|---|---|
| Met | Ala | Arg | Ser | Leu | Thr | Trp | Gly | Cys | Cys | Pro | Trp | Cys | Leu | Thr | Glu |
| 1 | | | | 5 | | | | | 10 | | | | | 15 | |
| Glu | Glu | Lys | Thr | Ala | Ala | Arg | Ile | Asp | Gln | Glu | Ile | Asn | Arg | Ile | Leu |
| | | | 20 | | | | | 25 | | | | | 30 | | |
| Leu | Glu | Gln | Lys | Lys | Gln | Glu | Arg | Glu | Glu | Leu | Lys | Leu | Leu | Leu | Leu |
| | | 35 | | | | | 40 | | | | | 45 | | | |
| Gly | Pro | Gly | Glu | Ser | Gly | Lys | Ser | Thr | Phe | Ile | Lys | Gln | Met | Arg | Ile |
| | 50 | | | | | 55 | | | | | 60 | | | | |
| Ile | His | Gly | Val | Gly | Tyr | Ser | Glu | Glu | Asp | Arg | Arg | Ala | Phe | Arg | Leu |
| 65 | | | | | 70 | | | | | 75 | | | | | 80 |

```
Leu Ile Tyr Gln Asn Ile Phe Val Ser Met Gln Ala Met Ile Asp Ala
            85                  90                  95

Met Asp Arg Leu Gln Ile Pro Phe Ser Arg Pro Asp Ser Lys Gln His
            100                 105                 110

Ala Ser Leu Val Met Thr Gln Asp Pro Tyr Lys Val Ser Thr Phe Glu
            115                 120                 125

Lys Pro Tyr Ala Val Ala Met Gln Tyr Leu Trp Arg Asp Ala Gly Ile
            130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Ser Glu Asp Ser Tyr Ile
            165                 170                 175

Pro Thr Ala Gln Asp Val Leu Arg Ser Arg Met Pro Thr Thr Gly Ile
            180                 185                 190

Asn Glu Tyr Cys Phe Ser Val Lys Lys Thr Lys Leu Arg Ile Val Asp
            195                 200                 205

Val Gly Gly Gln Arg Ser Glu Arg Arg Lys Trp Ile His Cys Phe Glu
            210                 215                 220

Asn Val Ile Ala Leu Ile Tyr Leu Ala Ser Leu Ser Glu Tyr Asp Gln
225                 230                 235                 240

Cys Leu Glu Glu Asn Asp Gln Glu Asn Arg Met Glu Glu Ser Leu Ala
            245                 250                 255

Leu Phe Ser Thr Ile Leu Glu Leu Pro Trp Phe Lys Ser Thr Ser Val
            260                 265                 270

Ile Leu Phe Leu Asn Lys Thr Asp Ile Leu Glu Asp Lys Ile His Thr
            275                 280                 285

Ser His Leu Ala Thr Tyr Phe Pro Ser Phe Gln Gly Pro Arg Arg Asp
            290                 295                 300

Ala Glu Ala Ala Lys Ser Phe Ile Leu Asp Met Tyr Ala Arg Val Tyr
305                 310                 315                 320

Ala Ser Cys Ala Glu Pro Gln Asp Gly Gly Arg Lys Gly Ser Arg Ala
            325                 330                 335

Arg Arg Phe Phe Ala His Phe Thr Cys Ala Thr Asp Thr Gln Ser Val
            340                 345                 350

Arg Ser Val Phe Lys Asp Val Arg Asp Ser Val Leu Ala Arg Tyr Leu
            355                 360                 365

Asp Glu Ile Asn Leu Leu
            370
```